United States Patent
Dreyfus et al.

(10) Patent No.: US 8,173,821 B2
(45) Date of Patent: May 8, 2012

(54) SEROTONIN AND NOREPINEPHRINE REUPTAKE INHIBITOR

(75) Inventors: Nicolas Jacques Francois Dreyfus, Basingstoke (GB); Sandra Ann Filla, Franklin, IN (US); Anette Margareta Johansson, Indianapolis, IN (US); Thierry J. Masquelin, Westfield, IN (US); Jikesh Arvind Shah, Greenwood, IN (US); Eric George Tromiczak, Indianapolis, IN (US); Magnus Wilhelm Walter, Basingstoke (GB)

(73) Assignee: Eli Lilly and Company, Indianapolis, IN (US)

( * ) Notice: Subject to any disclaimer, the term of this patent is extended or adjusted under 35 U.S.C. 154(b) by 197 days.

(21) Appl. No.: 12/754,800

(22) Filed: Apr. 6, 2010

(65) Prior Publication Data

US 2010/0261762 A1 Oct. 14, 2010

Related U.S. Application Data

(60) Provisional application No. 61/168,079, filed on Apr. 9, 2009.

(51) Int. Cl.
*C07D 213/62* (2006.01)
*A61K 31/44* (2006.01)

(52) U.S. Cl. ........................ 546/300; 514/335

(58) Field of Classification Search ................... None
See application file for complete search history.

(56) References Cited

U.S. PATENT DOCUMENTS

| | | |
|---|---|---|
| 2002/0151712 A1 | 10/2002 | Lin et al. |
| 2005/0245519 A1 | 11/2005 | Barta et al. |

FOREIGN PATENT DOCUMENTS

| | | |
|---|---|---|
| WO | WO9825920 | 6/1998 |
| WO | WO9932480 | 7/1999 |
| WO | WO0119817 A2 | 3/2001 |
| WO | 2005105763 A1 | 11/2005 |
| WO | WO2008/023258 A1 | 2/2008 |
| WO | WO2008070692 A2 | 6/2008 |
| WO | WO2010011811 A2 | 1/2010 |

OTHER PUBLICATIONS

Paul V. Fish, et al., Bioorganic & Medicinal Chemistry Letters, Vol, 19; pp. 2829-2834 (2009), 4-Piperidines and 3-pyrrolidines as dual serotonin and noradrenaline reuptake inhibitors: Design, synthesis and structure-activity relationships.

Kurt Kroenke, et al., General Hospital Pyschiatric vol., 31; pp. 206-219 (2009), Pharmacotherapy of chronic pain: a synthesis of recommendations from systematic reviews.

Aurelio Orjales, et al., Journal of Medicinal Chemistry vol. 46(25) pp. 5512-5532 (2003) Syntheses and Binding Studies of New [(Aryl)(aryloxy) methyl]piperidine. Derivatives and Related Compounds as Potential Antidepressant Drugs with High Affinity for Serotonin (5-HT) and Norepinephrine (NE) Transporters).

Mark W. Holladay, et al., Bioorganic & Medicinal Chemistry Letters, vol. 8; pp. 2797-2802 (1998), Structure-activity studies related to ABT-594, A Potent Nonopioid Analgesic Agent: Effect of Pyridine and Azetidine Ring Substitutions on Nicotinic Acetylcholine Receptor Binding Affinity and Analgesic Activity in Mice.

*Primary Examiner* — Janet Andres
*Assistant Examiner* — Heidi Reese
(74) *Attorney, Agent, or Firm* — R. Craig Tucker

(57) ABSTRACT

A serotonin and norepinephrine reuptake inhibitor of the formula:

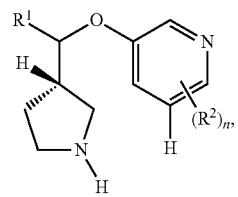

its uses, and methods for its preparation are described.

10 Claims, No Drawings

SEROTONIN AND NOREPINEPHRINE REUPTAKE INHIBITOR

This application claims priority to U.S. provisional application Ser. No. 61/168,079, filed Apr. 9, 2009.

Serotonin and norepinephrine have been implicated as modulators of endogenous analgesic mechanisms in descending pain pathways and serotonin norepinephrine reuptake inhibitors (SNRI's) have shown efficacy in the treatment of chronic painful conditions such as diabetic peripheral neuropathic pain and fibromyalgia (Kroenke et al. *Pharmacotherapy of chronic pain: a synthesis of recommendations from systematic reviews*, General Hospital Psychiatry 31 (2009) 206-219 (online at http://www.sciencedirect.com, accessed 30 Mar. 2009).

WO 2008/023258 describes certain 3-(pyrid-3-yloxymethyl)-piperidine compounds as monoamine reuptake inhibitors (serotonin and/or norepinephrine reuptake inhibitors) for the treatment of a wide range of disorders including pain.

US 20020151712 describes certain 3-pyrrolidinyl-oxy-3'-pyridyl ether compounds as nicotinic acetylcholine receptor ligands for various indications including the treatment of pain.

The present invention provides additional SNRI compounds with greater potency and higher selectivity for serotonin and norepinephrine reuptake than prior cited references. Additionally, certain of the present compounds provide an improved balance of serotonin vs. norepinephrine reuptake inhibitor activity compared to prior cited references. Namely, prior dual activity compounds typically have greater serotonin compared to norepinephrine reuptake inhibitor activity, whereas certain of the presently claimed compounds have dual activities significantly closer to the same levels for both serotonin and norepinephrine reuptake inhibition. Furthermore, the compounds of the present invention provide reduced acid lability, which is generally an advantage for improved pharmacological exposures as well as for ease of formulation. Yet further, certain of the compounds of the present invention provide improved metabolic degradation profiles which is generally an advantage for improved therapeutic exposures and may be advantageous in the reduction of pharmacological variability within a patient population.

The present invention provides compounds of Formula I:

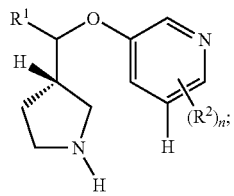

I or a pharmaceutically acceptable salt thereof,
wherein $R^1$ is selected from the group consisting of n-propyl, isobutyl, $(C_3-C_4)$cycloalkyl, and $(C_3-C_4)$cycloalkyl-methyl-;
n is 1 or 2; and
each $R^2$ is independently selected from the group consisting of fluoro, chloro, bromo, methyl, ethyl, trifluoromethyl, methoxy, ethoxy, cyclopropylmethyloxy, trifluoromethoxy, methylamino, cyclopropylamino and t-butyl-carbonylamino, provided that when n is 2, at least one of $R^2$ is fluoro, chloro, bromo, methyl, ethyl, trifluoromethyl, methoxy, or ethoxy.

The invention further provides a pharmaceutical composition comprising a compound of Formula I or a pharmaceutically acceptable salt thereof, in combination with a pharmaceutically acceptable carrier, diluent, or excipient. Furthermore, this invention provides a pharmaceutical composition adapted for the treatment of chronic pain comprising a compound of Formula I or a pharmaceutically acceptable salt thereof in combination with one or more pharmaceutically acceptable excipients, carriers, or diluents thereof Further embodiments provide a pharmaceutical composition adapted for the treatment of any one of diabetic peripheral neuropathic pain, fibromyalgia, pain associated with fibromyalgia, and inflammatory pain, as for example polymyalgia, rheumatoid arthritis or osteoarthritis, comprising a compound of Formula I or a pharmaceutically acceptable salt thereof in combination with one or more pharmaceutically acceptable excipients, carriers, or diluents thereof The present invention also provides a method of treating chronic pain in a mammal comprising administering to a mammal in need of such treatment an effective amount of a compound of Formula I or a pharmaceutically acceptable salt thereof Particular embodiments of this aspect of the invention include a method of treating diabetic peripheral neuropathic pain, a method of treating fibromyalgia, a method of treating pain associated with fibromyalgia, and/or a method of treating inflammatory pain, as for example polymyalgia, rheumatoid arthritis or osteoarthritis, each method individually comprising administering to a mammal in need of such treatment an effective amount of a compound of Formula I, or a pharmaceutically acceptable salt thereof In one particular embodiment of this aspect of the invention, the mammal is a human.

This invention also provides a compound of Formula I or a pharmaceutically acceptable salt thereof for use in therapy. Within this aspect, the invention provides a compound of Formula I, or a pharmaceutically acceptable salt thereof, for use in the treatment of chronic pain in mammals, particularly humans. Further embodiments of this aspect of the invention include any one of the following: a compound of Formula I, or a pharmaceutically acceptable salt thereof, for use in the treatment of chronic pain; a compound of Formula I, or a pharmaceutically acceptable salt thereof, for use in the treatment of diabetic peripheral neuropathic pain; a compound of Formula I, or a pharmaceutically acceptable salt thereof, for use in the treatment of fibromyalgia; a compound of Formula I, or a pharmaceutically acceptable salt thereof, for use in the treatment of pain associated with fibromyalgia; a compound of Formula I, or a pharmaceutically acceptable salt thereof, for use in the treatment of inflammatory pain; a compound of Formula I, or a pharmaceutically acceptable salt thereof, for use in the treatment of polymyalgia; a compound of Formula I, or a pharmaceutically acceptable salt thereof, for use in the treatment of rheumatoid arthritis; and a compound of Formula I, or a pharmaceutically acceptable salt thereof, for use in the treatment of osteoarthritis.

Another aspect of this invention provides the use of a compound of Formula I, or a pharmaceutically acceptable salt thereof, in the manufacture of a medicament for the treatment of chronic pain. Particular embodiments of this aspect include use of a compound of Formula I, or a pharmaceutically acceptable salt thereof, in the manufacture of a medicament for the treatment of diabetic peripheral neuropathic pain; use of a compound of Formula I, or a pharmaceutically acceptable salt thereof, in the manufacture of a medicament for the treatment of fibromyalgia; use of a compound of Formula I, or a pharmaceutically acceptable salt thereof, in the manufacture of a medicament for the treatment of pain associated with fibromyalgia; use of a compound of Formula I, or a pharmaceutically acceptable salt thereof, in the manufacture of a medicament for the treatment of inflammatory pain; use of a compound of Formula I, or a pharmaceutically acceptable salt thereof, in the manufacture of a medicament for the treatment of polymyalgia; use of a compound of Formula I, or a pharmaceutically acceptable salt thereof, in the manufacture of a medicament for the treatment of rheumatoid arthritis; and use of a compound of Formula I, or a pharmaceutically acceptable salt thereof, in the manufacture of a medicament for the treatment of osteoarthritis.

Compounds of this invention are bases, and accordingly react with a number of organic and inorganic acids to form pharmaceutically acceptable salts and the present invention includes the pharmaceutically acceptable salts of a compound of Formula I. The term "pharmaceutically acceptable salt" as used herein, refers to any salt of a compound of Formula I that is substantially non-toxic to living organisms. Such salts include those listed in *Journal of Pharmaceutical Science,* 66, 2-19 (1977), which are known to the skilled artisan.

Persistent pain is caused by chronic pathologic processes in somatic structures or viscera, or by prolonged and sometimes permanent dysfunction of the peripheral or central nervous system, or by both. Persistent inflammation, tissue damage, or nerve injury, results in hyperexcitability of dorsal horn neurons within the spinal cord, a process also known as central sensitization. Central sensitization is characterized by altered responsiveness of dorsal horn neurons, the expansion of receptive fields, and plasticity of neuronal connections within the pain transmitting pathways. These processes lead to increased neuronal activity within ascending pain pathways and supraspinal sites and/or to dysfunction/disinhibition of the endogenous spinal and supraspinal descending pain inhibitory mechanisms.

Central sensitization and disinhibition can produce an ongoing condition of spontaneous, persistent pain as well as an increased sensitivity to painful stimuli (hyperalgesia) or to painful experience of normally non-painful mechanical or thermal stimuli (allodynia). C. J. Woolf, *Pain: Moving from Symptom Control toward Mchanism-Specific Pharmacologic Management,* Annals of Internal Medicine, 140, 441-451 (2004). These processes are postulated to underlie several types of persistent or chronic pain, including neuropathic pain (including diabetic neuropathy, infectious neuropathic pain associated with AIDS, non-surgical carpal tunnel syndromes, post-herpetic neuralgia, cervical, thoracic and lumbosacral radiculopathies, trigeminal neuralgia, complex regional pain syndromes I and II, chemotherapy-induced neuropathic pain and central neuropathic pain syndromes including spinal cord injury, multiple sclerosis or stroke-related pain), inflammatory pain (including polymyalgia, rheumatoid arthritis and osteoarthritis), and non-neuropathic non-inflammatory pain (including chronic fatigue syndrome, chronic back pain without radiculopathy, fibromyalgia, chronic tension type headaches, inflammatory bowel disorders, irritable bowel syndrome, whiplash injuries, chronic pelvic pain including interstitial cystitis, and temporomandibular joint disorder (TMJD)).

The recognition of the correlation between disinhibition and an imbalance of serotonin and norepinephrine in endogenous pain inhibitory pathways led to the successful evaluation of serotonin and norepinphrine reuptake inhibitors in the treatment of chronic pain conditions in man. Therefore, as dual activity inhibitors of both serotonin and norepinephrine reuptake, the compounds of Formula I are useful for the treatment of chronic pain, including diabetic peripheral neuropathic pain and fibromyalgia, in mammals. In one preferred embodiment, the mammal is a human. Furthermore, the compounds of Formula I are useful for the treatment of depressive disorders (including major depressive disorder), anxiety disorders (including generalized anxiety disorder), and incontinence (such as urge, stress and mixed-type incontinence). (Orjales, et al., *Journal of Medicinal Chemistry,* 46(25), 5512-5532 (2003); Fish, et al., *Bioorganic and Medicinal Chemistry Letters,* 17, 2022-2025 (2007))

Abbreviations used herein are defined as follows:
"HPLC" means high-pressure liquid chromatography.

"MS (ES+)" means mass spectroscopy using electrospray ionization.
"MTBE" means methyl t-butyl ether.
"NMR" means nuclear magnetic resonance.
"THF" means tetrahydrofuran.
"EtOAc" means ethyl acetate.
"MeOH" mean methanol
"DMSO" means dimethyl sulfoxide.
"SCX column" means strong cation exchange column.
"Pd(OAc)$_2$" means Palladium(II) acetate.
"DMF" means dimethylformamide.
"n-BuLi" means n-butyllithium
"MeOAc" means methyl acetate.
"(S)—Ru(OAc)$_2$T-BINAP" means diacetato[(S)-(−)-2,2'-bis(di-p-tolylphosphino)-1,1'-binaphthyl]ruthenium(II)
"DMA" means dimethylacetamide.
"XRD" means X-Ray Diffraction.
"TOCSY" means Total Correlation Spectroscopy.
"SERT" means serotonin transporter.
"hSERT" means human serotonin transporter.
"Net" means norepinephrine transporter.
"hNet" means human norepinephrine transporter.
"DAT" means dopamine transporter.
"hDAT" means human dopamine transporter.
"HEPES" means 4-(2-hydroxyethyl)-1-piperazineethanesulfonic acid.
"SEM" means standard errors of means.
"PCA" means para-chloroamphetamine.
"α-MMT" means Alpha-methyl-m-tyrosine.
"IC$_{50}$" means half maximal inhibitory concentration.
"ED$_{50}$" means effective dose.

Preferred compounds of the present invention are compounds wherein:
1) $R^1$ is n-propyl or isobutyl (i.e. 2-methylpropyl-);
2) $R^1$ is isobutyl (i.e. 2-methylpropyl-);
3) $R^1$ is n-propyl;
4) $R^1$ is (C$_3$-C$_4$)cycloalkyl or (C$_3$-C$_4$)cycloalkyl-methyl-;
5) $R^1$ is cyclopropyl or cyclopropylmethyl;
6) $R^1$ is cyclobutyl or cyclobutylmethyl;
7) each $R^2$ is independently selected from chloro, bromo, methyl, ethyl, trifluoromethyl, methoxy, ethoxy, cyclopropylmethyloxy, and trifluoromethoxy;
8) each $R^2$ is independently selected from chloro, bromo, methyl, ethyl, and methoxy;
9) each $R^2$ is independently selected from chloro, methyl, and methoxy;
10) each $R^2$ is independently selected from methyl, ethyl, and methoxy;
11) $R^1$ is isobutyl and each $R^2$ is independently selected from chloro, bromo, methyl, ethyl, trifluoromethyl, methoxy, ethoxy, cyclopropylmethyloxy, and trifluoromethoxy;
12) $R^1$ is isobutyl and each $R^2$ is independently selected from chloro, bromo, methyl, ethyl, and methoxy;
13) $R^1$ is isobutyl and each $R^2$ is independently selected from chloro, methyl, and methoxy;
14) $R^1$ is isobutyl and each $R^2$ is independently selected from methyl, ethyl, and methoxy;
15) $R^1$ is n-propyl and each $R^2$ is independently selected from chloro, bromo, methyl, ethyl, trifluoromethyl, methoxy, ethoxy, cyclopropylmethyloxy, and trifluoromethoxy;
16) $R^1$ is n-propyl and each $R^2$ is independently selected from chloro, bromo, methyl, ethyl, and methoxy;
17) $R^1$ is n-propyl and each $R^2$ is independently selected from chloro, methyl, and methoxy;

18) $R^1$ is n-propyl and each $R^2$ is independently selected from methyl, ethyl, and methoxy;
19) $R^1$ is $(C_3-C_4)$cycloalkyl or $(C_3-C_4)$cycloalkyl-methyl- and each $R^2$ is independently selected from chloro, bromo, methyl, ethyl, trifluoromethyl, methoxy, ethoxy, cyclopropylmethyloxy, and trifluoromethoxy;
20) $R^1$ is $(C_3-C_4)$cycloalkyl or $(C_3-C_4)$cycloalkyl-methyl- and each $R^2$ is independently selected from chloro, bromo, methyl, ethyl, and methoxy;
21) $R^1$ is $(C_3-C_4)$cycloalkyl or $(C_3-C_4)$cycloalkyl-methyl- and each $R^2$ is independently selected from chloro, methyl, and methoxy;
22) $R^1$ is $(C_3-C_4)$cycloalkyl or $(C_3-C_4)$cycloalkyl-methyl-, n is 1 or 2 and each $R^2$ is independently selected from methyl, ethyl, and methoxy;
23) $R^1$ cyclopropyl or cyclopropylmethyl, n is 1 or 2 and each $R^2$ is independently selected from chloro, bromo, methyl, ethyl, trifluoromethyl, methoxy, ethoxy, cyclopropylmethyloxy, and trifluoromethoxy;
24) $R^1$ cyclopropyl or cyclopropylmethyl, n is 1 or 2 and each $R^2$ is independently selected from chloro, bromo, methyl, ethyl, and methoxy;
25) $R^1$ cyclopropyl or cyclopropylmethyl, n is 1 or 2 and each $R^2$ is independently selected from chloro, methyl, and methoxy;
26) $R^1$ cyclopropyl or cyclopropylmethyl, n is 1 or 2 and each $R^2$ is independently selected from methyl, ethyl, and methoxy;
27) $R^1$ is cyclobutyl or cyclobutylmethyl, n is 1 or 2 and each $R^2$ is independently selected from chloro, bromo, methyl, ethyl, trifluoromethyl, methoxy, ethoxy, cyclopropylmethyloxy, and trifluoromethoxy;
28) $R^1$ is cyclobutyl or cyclobutylmethyl, n is 1 or 2 and each $R^2$ is independently selected from chloro, bromo, methyl, ethyl, and methoxy;
29) $R^1$ is cyclobutyl or cyclobutylmethyl, n is 1 or 2 and each $R^2$ is independently selected from chloro, methyl, and methoxy;
30) $R^1$ is cyclobutyl or cyclobutylmethyl, n is 1 or 2 and each $R^2$ is independently selected from methyl, ethyl, and methoxy;
31) For each of above recited embodiments 7 through 30, further preferred compounds are those wherein n is 2 and the $R^2$ substituents are substituted at the pyridyl 2 and 6 positions.

One particularly preferred compound of the present invention is (3S)-3-((S)1-(6-methoxy-2-methyl-3-pyridyloxy)-3-methyl-butyl)-pyrrolidine, or a pharmaceutically acceptable salt thereof, as for example the L- and/or D-tartrate salt, as exemplified in examples 19, 19A, and 19B.

There are two chiral centers in the compounds of Formula I, each of which is marked with "*" below:

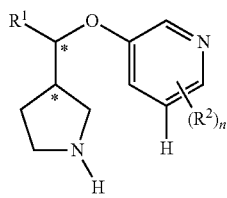

The compounds of Formula I may, therefore, exist in a variety of stereoisomeric configurations, such as a racemate, as well as the diastereomers and enantiomers. Activity of the compounds is significantly improved for compounds wherein the chiral center at the 3-position of the pyrrolidine ring exists in the "S" absolute configuration as required in Formula I. Compounds may have the chiral center at the 1'-position of the appended chain in either the "R" absolute configuration, the "S" absolute configuration, or any mixture thereof:

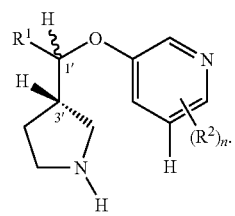

Generally, stereochemically pure compounds are preferred over racemates. Generally one stereoisomer has enhanced activity over the other. Preferred compounds are those with both chiral centers in the "S" absolute configuration:

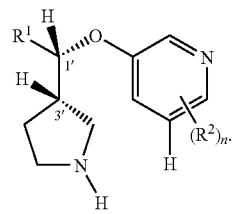

The specific stereoisomers and enantiomers of the compound of Formula I may be prepared by one of ordinary skill in the art utilizing well known techniques and processes, such as those disclosed by J. Jacques, et al., "Enantiomers, Racemates, and Resolutions", John Wiley and Sons, Inc., 1981, and E. L. Eliel and S. H. Wilen, "Stereochemistry of Organic Compounds", (Wiley-Interscience 1994), and European Patent Application No. EP-A-838448, published Apr. 29, 1998. Examples of resolutions include recrystallization techniques or chiral chromatography.

The compounds of the present invention can be prepared according to the following synthetic schemes by methods well known and appreciated in the art. Suitable reaction conditions for the steps of these schemes are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical. The particular order of steps required to produce the compounds of the present invention is dependent upon the particular compound being synthesized, the starting compound, and the relative liability of the selected substituents, as is well appreciated by the skilled chemist. Substituents $R^1$ and $R^2$, unless otherwise indicated, are as previously defined, and all reagents are well known and appreciated in the art. Pg is a nitrogen protecting group, such as those well known in the art (see Wuts and Greene, *Greene's Protective Groups in Organic Synthesis*, 4th Ed., Chapter 7, John Wiley and Sons Inc., (2007).

Scheme 1

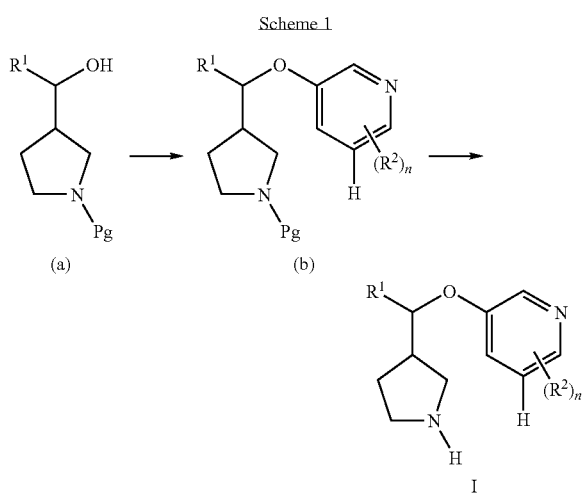

The starting alcohol (a) is reacted with a suitable base such as sodium hydride and an appropriately substituted aryl fluoride in a suitable solvent, such as dimethyl sulfoxide, at elevated temperature to provide the ether (b). Alternatively, alcohol (a) may be reacted with an appropriately substituted pyridine under standard Mitsunobu conditions to provide the ether (b). The ether (b) is then de-protected under conditions well known to the skilled artisan to provide the compound of Formula I. (For example, see: Greene and Wuts, supra). The resulting amine may then be treated with pharmaceutically acceptable acids, such as L-tartaric acid, D-tartaric acid, or HCl, in a suitable solvent, such as methanol, to provide the pharmaceutically acceptable salts of the compounds of Formula I.

The requisite alcohol (a) may be prepared as described in the following scheme where $R^1$, $R^2$ and Pg are as previously defined.

An N-protected pyrrolidine-3-carboxylic acid (c) is reacted with N,O-dimethyl-hydroxylamine under standard amide coupling conditions to provide the Weinreb amide (d). This amide is reacted with a suitable organometallic nucleophile to provide the ketone (e). Reduction of the ketone (e) under standard conditions, such as with sodium borohydride in methanol, provides the alcohol (a). Alternatively, an N-protected 2-pyrrolidinone (f) may be treated with a suitable base, such as lithium bis(trimethylsilyl)amide in a suitable solvent, such as tetrahydrofuran, and the resulting anion is reacted with an aldehyde to provide the addition product (g). The amide moiety is reduced under standard conditions, such as by reaction with boron-methyl sulfide in tetrahydrofuran at elevated temperature to provide alcohol (a).

The introduction of the 6-methoxy group into 6-methoxy-2-methyl-3-pyridyloxy pyrrolidine derivatives may be accomplished on the free amine of the corresponding 6-chloro-2-methyl-3-pyridyloxy derivatives by nucleophilic displacement of the chloro by a methoxide under standard nucleophilic aromatic substitution conditions to provide the desired compound as shown in Scheme 3.

Scheme 3

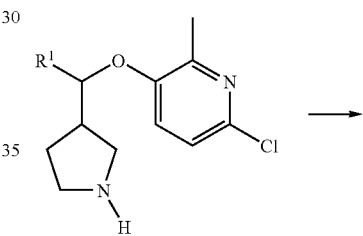

Scheme 2

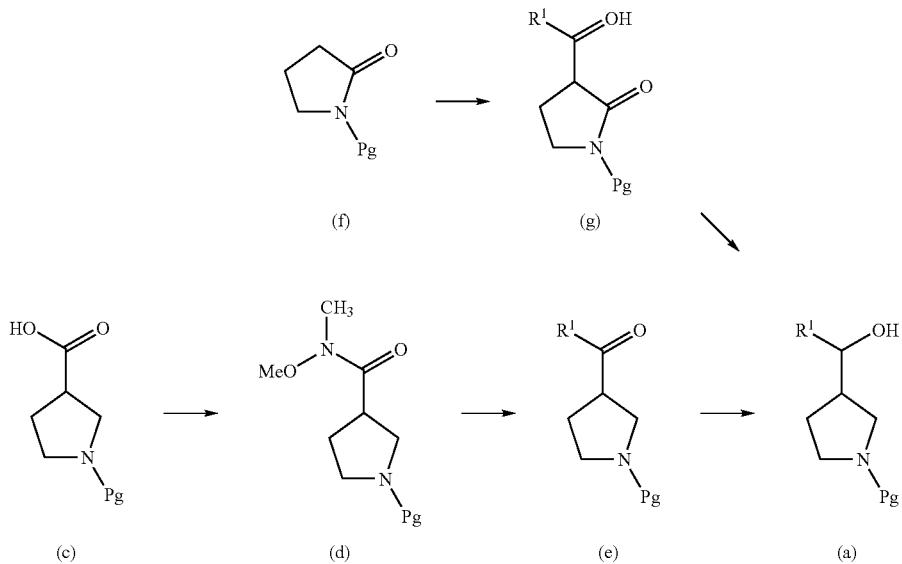

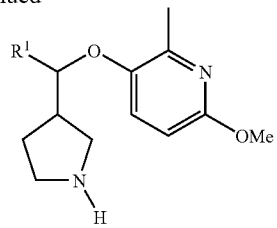

In the following preparations and examples, the designation (S-mix) is taken to represent an intermediate or compound of Formula I wherein the chiral center at the 3-position of the pyrrolidine ring is in the "S" absolute configuration and the second chiral center (referred to as 1' above) is a mixture of "S" and "R". The designation (S-1) is taken to represent that the corresponding intermediate or compound of Formula I is either the first eluting enantiomer or is derived from the first eluting enantiomer when the mixture of enantiomers was separated by chromatography. Similarly, the designation (S-2) is taken to represent that the corresponding intermediate or compound of Formula I is either the second eluting enantiomer or is derived from the second eluting enantiomer when the mixture of enantiomers was separated by chromatography. The designation (D1) is taken to represent an intermediate or compound of Formula I that is, or is derived from, the first eluting diastereomer when the diastereomers were separated by chromatography. Likewise, the designation (D2) is taken to represent an intermediate or compound of Formula I that is, or is derived from, the second eluting diastereomer when the diastereomers were separated by chromatography. The designations (D1-E1) and (D1-E2) are taken to represent an intermediate or compound of Formula I that is, or is derived from, the first and second eluting enantiomers, respectively, of the first-eluting diastereomer. Likewise, the designations (D2-E1) and (D2-E2) are taken to represent an intermediate or compound of Formula I that is, or is derived from, the first and second eluting enantiomers, respectively, of the second-eluting diastereomer. The exception from these general rules is when a Mitsunobu reaction has been undertaken with alcohol (a) leading to inversion of the configuration of the 1' carbon. In those examples the designation of a starting alcohol of (S-1) results in an (S-2) product and a (D1) starting alcohol results in a (D2) product.

The following Preparations and Examples are illustrative of methods useful for the synthesis of the compounds of the present invention. The names for many of the compounds illustrated in the preparations and examples are provided from structures drawn with ChemDraw Ultra 10.0.

Preparation 1:
(S)-3-(3-Methylbutanoyl)pyrrolidine-1-carboxylic acid tert-butyl ester

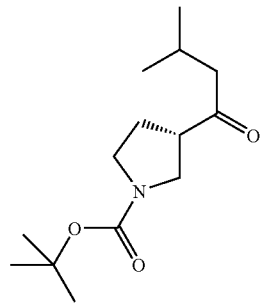

(S)-3-(Methoxy(methyl)carbamoyl)-pyrrolidine-1-carboxylic acid tert-butyl ester

Add 1,1'-carbonyldiimidazole (414.33 g, 2.56 mol) portion wise to a stirred solution of (S)-N-tert-butoxycarbonylpyrrolidine-3-carboxylic acid (500 g, 2.32 mol) in dichloromethane (5.81 L) and stir at room temperature under nitrogen for 1 hour. Add N,O-di-methylhydroxylamine hydrochloride (253.04 g, 2.56 mol) and stir at room temperature for 48 hours. Quench the reaction with 1N HCl, and extract with ethyl acetate (2×). Wash the combined organics with saturated $NaHCO_3$ and brine. Dry ($MgSO_4$), filter and concentrate under reduced pressure to provide 535 g (89%) of the title compound. MS (m/z)=203 (M−55).

Addition of Grignard to Weinreb Amide

Add a solution of isobutylmagnesium bromide (2.0 M in tetrahydrofuran (THF), 63.47 mL, 126.94 mmol) in THF (50 mL) drop wise to a stirred solution of (S)-3-(methoxy(methyl)carbamoyl)-pyrrolidine-1-carboxylic acid tert-butyl ester (21.86 g, 84.62 mmol) in THF (400 mL) kept under nitrogen at −7° C. Stir an hour at −5° C. then allow the reaction to warm to room temperature and continue to stir overnight. Add saturated aqueous ammonium chloride and extract with ethyl acetate (2×). Dry ($MgSO_4$), filter and concentrate under reduced pressure. Purify the residue by silica gel chromatography, eluting with ethyl acetate (EtOAc) in hexane, (0-20% gradient) to provide 21.6 g (99.6%) of the title compound.

The compounds of Preparations 2-5 are prepared essentially as described in Preparation 1.

| Prep. | Compound | Structure | MS (m/z) |
|---|---|---|---|
| 2 | (S)-3-But-3-enoylpyrrolidine-1-carboxylic acid tert-butyl ester | 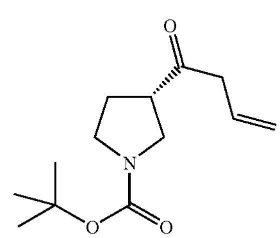 | |

| Prep. | Compound | Structure | MS (m/z) |
|---|---|---|---|
| 3 | (S)-3-Cyclopropylcarbonyl-pyrrolidine-1-carboxylic acid tert-butyl ester | 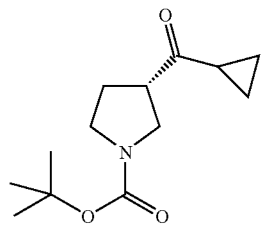 | 262 (M + 23) |
| 4 | (S)-3-Butanoyl-pyrrolidine-1-carboxylic acid tert-butyl ester | 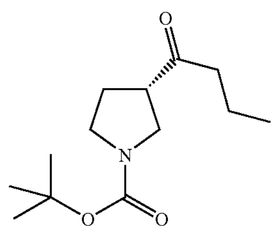 | 264 (M + 23) |

Preparation 5: (S)-3-Cyclobutylcarbonyl-pyrrolidine-1-carboxylic acid tert-butyl ester

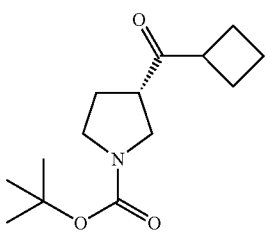

Add diisobutylaluminium hydride (1M in toluene, 0.790 mL, 0.790 mmol) to a stirred mixture of magnesium (0.960 g, 39.5 mmol) and iodine (0.100 g, 0.395 mmol) in THF (1 mL) under nitrogen. Add drop wise a solution of cyclobutyl bromide (8.00 g, 59.2 mmol) in THF (10 mL) and stir the reaction at 60° C. for 2 h whereby all the magnesium is consumed. Cool the mixture to room temperature and add drop wise a solution of (S)-3-(methoxy(methyl)carbamoyl)-pyrrolidine-1-carboxylic acid tert-butyl ester (10.2 g, 39.5 mmol) in THF (50 mL). Stir the reaction mixture at room temperature for 2.5 h. Quench with 1 M aqueous citric acid, extract with EtOAc. Wash the organic layer with water and saturated aqueous NaCl, dry ($Na_2SO_4$), filter and concentrate under reduced pressure. Purify the residue by silica gel chromatography, eluting with EtOAc in hexanes (0-50% gradient) to obtain the title compound (5.30 g, 53%).

Preparation 6: (3S)-3-(1-Hydroxy-3-methyl-butyl)-pyrrolidine-1-carboxylic acid tert-butyl ester, isomer 1 (S-1) and isomer 2 (S-2)

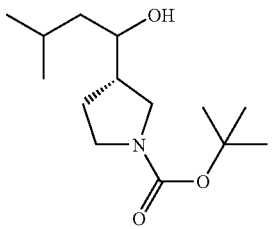

Add sodium borohydride (15.2 g, 423 mmol) to a solution of (S)-3-(3-methylbutanoyl)-pyrrolidine-1-carboxylic acid tert-butyl ester (21.6 g, 84.6 mmol) in methanol (500 mL) portion wise and stir at room temperature overnight. Add another equivalent of sodium borohydride (3.04 g, 84.6 mmol). Stir for another 2 hours, evaporate the methanol to half the volume, add brine and extract with EtOAc. Dry the combined organic phases ($MgSO_4$), filter and concentrate under reduced pressure. Separate the diastereoisomers by super critical fluid chromatography (AD-H column) eluting with 10% MeOH/$CO_2$ with 0.2% diethylmethylamine to provide (3S)-3-(1-hydroxy-3-methyl-butyl)-pyrrolidine-1-carboxylic acid tert-butyl ester, isomer 1 (S-1) as the first eluting isomer (8.2 g, 38%) and (3S)-3-(1-hydroxy-3-methyl-butyl)-pyrrolidine-1-carboxylic acid tert-butyl ester, isomer 2 (S-2) as the second eluting isomer (8.9 g, 41%).

Preparation 7: (3S)-3-(1-Hydroxy-butyl)-pyrrolidine-1-carboxylic acid tert-butyl ester, isomer 1 (S-1) and isomer 2 (S-2)

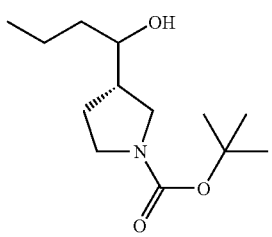

Add sodium borohydride (5.19 g, 145 mmol) portion wise to a solution of (S)-3-butanoyl-pyrrolidine-1-carboxylic acid tert-butyl ester (7.0 g, 29.0 mmol) in methanol (200 mL) and stir at room temperature over night. Add more sodium borohydride (1.4 g, 39 mmol) and stir an hour at room temperature. Evaporate the methanol to half volume, add brine and extract with ethyl acetate. Dry the combine organic phases (MgSO₄), filter and concentrate under reduced pressure. Separate the diastereoisomers by silica gel chromatography eluting with 5% isopropylamine in hexanes to provide (3S)-3-(1-hydroxy-butyl)-pyrrolidine-1-carboxylic acid tert-butyl ester, isomer 1 (S-1) as the first eluting isomer (2.6 g, 37%) and (3S)-3-(1-hydroxy-butyl)-pyrrolidine-1-carboxylic acid tert-butyl ester, isomer 2 (S-2) as the second eluting isomer (1.8 g, 26%)

The compounds of Preparations 8-9 may be prepared essentially as described in Preparation 8.

| Prep. | Compound | Structure | MS (m/z) |
|---|---|---|---|
| 8 | (3S)-3-(Cyclopropyl(hydroxy)methyl)pyrrolidine-1-carboxylic acid tert-butyl ester, isomer 1 (S-1) | 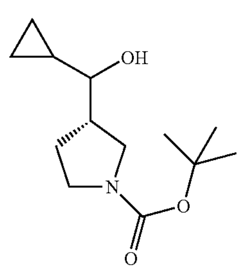 | |
| 9 | (3S)-3-(Cyclopropyl(hydroxy)methyl)pyrrolidine-1-carboxylic acid tert-butyl ester, isomer 2 (S-2) | 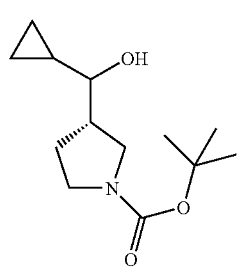 | |

Preparation 10: (3S)-3-(Cyclobutyl-hydroxy-methyl)-pyrrolidine-1-carboxylic acid tert-butyl ester (S-mix)

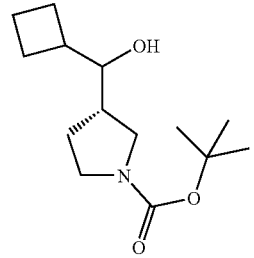

Add sodium borohyride (1.19 g, 31.4 mmol) to a stirred solution of (S)-3-cyclobutanecarbonyl-pyrrolidine-1-carboxylic acid tert-butyl ester (5.30 g, 20.9 mmol) in MeOH (105 mL) kept under an atmosphere of nitrogen at 0° C. Stir the mixture for 2 hours while warming to room temperature. Concentrate the MeOH, dilute with dichloromethane and wash the organics with saturated aqueous NaHCO₃, water and brine. Dry (MgSO₄), filter and concentrate under reduced pressure to yield the title compound (4.4 g, 82%) as a mixture of diastereomers (S-mix).

Preparation 11: (3S)-3-(1-Hydroxy-3-butenyl)-pyrrolidine-1-carboxylic acid tert-butyl ester, (S-mix)

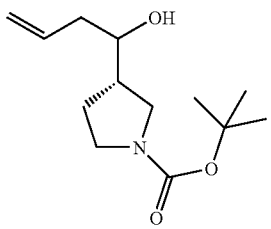

The compound of Preparation 11 may be prepared essentially as described in Preparation 10, using (3S)-3-(but-3-enonyl)-pyrrolidine-1-carboxylic acid tert-butyl ester.

Preparation 12: 3-(1-Hydroxy-3-methyl-butyl)-pyrrolidine-1-carboxylic acid tert-butyl ester, diastereomer 1 (D1)

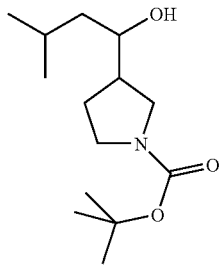

3-(1-Hydroxy-3-methyl-butyl)-2-oxo-pyrrolidine-1-carboxylic acid tert-butyl ester, diastereomer 1 (D1) and diastereomer 2 (D2)

Add lithium bis(trimethyl silyl)-amide (1.0 M in THF, 148 mL, 148 mmol) to a solution of 2-oxo-pyrrolidine-1-carboxylic acid tert-butyl ester (25.0 g, 134 mmol) in THF (450 mL) at −78° C. and stir under nitrogen for 2 hours. Add 3-methylbutyraldehyde (17.5 mL, 162 mmol) followed by boron trifluoride diethyl etherate (20.5 mL, 162 mmol) and continue to stir at −78° C. for 2 hours. Warm the mixture to room temperature, quench with saturated aqueous ammonium chloride (250 mL) and extract with EtOAc (3×). Dry the combined organics (Na$_2$SO$_4$), filter and concentrate under reduced pressure. Divide the crude product into two equal portions and purify each portion by silica gel chromatography, eluting with 0-40% EtOAc in hexanes to provide 3-(1-hydroxy-3-methyl-butyl)-2-oxo-pyrrolidine-1-carboxylic acid tert-butyl ester, diastereomer 1 (12.5 g, 34%) (D1) as the first eluting isomer, MS (m/z)=216.0 (M−56), and 3-(1-hydroxy-3-methyl-butyl)-2-oxo-pyrrolidine-1-carboxylic acid tert-butyl ester, diastereomer 2 (3.87 g, 11%) (D2) as the second eluting isomer. MS (m/z)=216.0 (M−56)

Amide Reduction,

Slowly add boron-methyl sulfide complex (2.0 M in THF, 68.8 mL, 138 mmol) to a solution of 3-(1-hydroxy-3-methyl-butyl)-2-oxo-pyrrolidine-1-carboxylic acid tert-butyl ester (D1) (12.5 g, 45.9 mmol) in THF (220 mL) kept under nitrogen. Heat the mixture to reflux for 2 hours and quench with saturated aqueous ammonium chloride (200 mL). Extract with ethyl acetate (2×). Wash the combined organics with H$_2$O (100 mL), 5% citric acid (100 mL) and brine (100 mL). Dry (Na$_2$SO$_4$), filter and concentrate under reduced pressure. Purify the residue by silica gel chromatography eluting with 0-40% of EtOAc in hexanes to yield 10.7 g (91%) of the title compound. MS (m/z)=202.0 (M−56).

Preparation 13: (3S)-3-(2-cyclopropyl-1-hydroxyethyl)pyrrolidine-1-carboxylic acid tert butyl ester (S-mix)

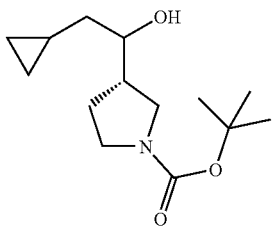

Add palladium (II) acetate (50.0 mg; 0.22 mmol) to a stirred solution of (3S)-tert-butyl 3-(1-hydroxybut-3-enyl)pyrrolidine-1-carboxylate (S-mix) (3.0 g, 12.43 mmol) and freshly prepared diazomethane (50 mL, about 23.8 mmol in diethyl ether) in THF (20 mL) under nitrogen at 0° C. (Caution: vigorous gas evolution). Stir at 0° C. for 10 minutes. Warm to room temperature, pour into water and extract with ethyl acetate (3×). Wash the combined organics with water and brine. Dry (MgSO$_4$), filter and concentrate under reduced pressure. Subject the residue to silica gel chromatography, eluting with 0-100% ethyl acetate in hexane to afford 2.9 g (91%) of the title compound. MS (m/z)=200.0 (M−55)

Preparation 14: 3-(2-Cyclobutyl-1-hydroxyethyl)pyrrolidine-1-carboxylic acid tert butyl ester

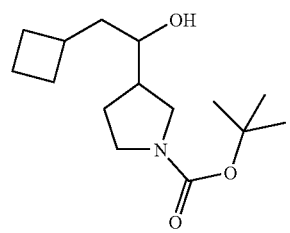

tert-Butyl 3-(2-(diethoxyphosphoryl)acetyl)pyrrolidine-1-carboxylate

Add butyl lithium (98.0 mL, 157 mmol) dropwise to a solution of diethyl methylphosphonate (23.6 g, 155 mmol) in THF (194 mL) under nitrogen at −78° C. over 15 minutes. Add (S)-3-(methoxy(methyl)carbamoyl)pyrrolidine-1-carboxylic acid tert butyl ester (5.0 g, 19.4 mmol) in THF and stir at −78° C. for about 3.5 hrs. Pour into water and extract with ethyl acetate (3×). Wash the combined organics with water and brine. Dry (MgSO$_4$), filter, and concentrate. Subject the residue to silica gel chromatography, eluting with 0-50% acetone in chloroform followed by another silica gel chromatography eluting with 0-30% acetone in dichloromethane to afford 3.15 g (47%) of the desired compound. MS (m/z)= 294.0 (M−55)

3-(2-Cyclobutylideneacetyl)pyrrolidine-1-carboxylic acid tert butyl ester

Add cyclobutanone (0.738 mL; 9.89 mmol) to a stirred mixture of 3-(2-(diethoxyphosphoryl)-acetyl)pyrrolidine-1-carboxylic acid tert butyl ester (3.14 g, 8.99 mmol) and potassium hydroxide (656 mg, 11.7 mmol) in ethanol (45 mL) kept under nitrogen at 5° C. Warm to room temperature and stir for 3 hours. Concentrate under reduced pressure and subject the residue to silica gel chromatography, eluting with 20% ethyl acetate in hexanes to afford 0.85 g (36%) of the crude desired compound, which is used in the next step without further purification.

3-(2-Cyclobutylacetyl)pyrrolidine-1-carboxylic acid tert butyl ester

Add palladium on carbon (50 mg, catalytic) to 3-(2-cyclobutylidene-acetyl)pyrrolidine-1-carboxylic acid tert butyl ester (850 mg, 3.20 mmol) in ethyl acetate (25 mL) and stir under nitrogen at room temperature. Install a balloon of hydrogen gas and stir overnight. Filter the reaction over celite, rinse with ethyl acetate and concentrate to dryness to afford 391 mg (46%) of the desired compound. MS (m/z)=212.0 (M−55)

Reduction

Add sodium borohydride (71.9 mg, 1.90 mmol) portion wise to 3-(2-cyclobutylacetyl)pyrrolidine-1-carboxylic acid tert butyl ester (391 mg, 1.46 mmol) in methanol (7.31 mL) at 0° C. Stir at room temperature overnight. Concentrate under reduced pressure, dilute with water and extract with ethyl acetate (3×). Wash the combined organics with saturated aqueous NaHCO$_3$, water and brine. Dry (MgSO$_4$), filter and concentrate under reduced pressure to yield 0.39 g (97%) of the title compound. MS (m/z)=214.0 (M−55)

Preparation 15: (3S)-3-[2-Cyclopropyl-1-(6-chloro-2-methyl-3-pyridyloxy)-ethyl]-pyrrolidine-1-carboxylic acid tert-butyl ester isomer 1 (S-1) and isomer 2 (S-2)

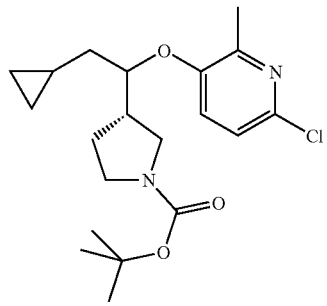

Add sodium hydride (60%, 94.0 mg, 2.35 mmol) slowly at room temperature to a mixture of (3S)-3-(2-cyclopropyl-1-hydroxy-ethyl)-pyrrolidine-1-carboxylic acid tert-butyl ester (S-mix) (31.5 g, 123.36 mmol) and DMSO (11.8 mL) kept under an atmosphere of nitrogen. Stir for 10 minutes and then add 2-chloro-5-fluoropicoline (359 mg, 2.47 mmol). Heat to 60° C. and stir overnight. Cool the mixture, pour into water and extract with ethyl acetate (3×). Wash the combined organic extracts with water and brine. Dry (MgSO$_4$), filter and concentrate. Purify the crude residue by silica gel chromatography, eluting with 20% ethyl acetate in hexane to afford (3S)-3-[2-cyclopropyl-1-(6-chloro-2-methyl-3-pyridyloxy)-ethyl]-pyrrolidine-1-carboxylic acid tert-butyl ester, isomer 1, (S-1) (99 mg, 22%) as the first eluting isomer and (3S)-3-[2-cyclopropyl-1-(6-chloro-2-methyl-3-pyridyloxy)-ethyl]-pyrrolidine-1-carboxylic acid tert-butyl ester, isomer 2, (S-2) (80 mg, 18%) as the second eluting isomer. MS (m/z)=325.0 (M−55)

The compounds of Preparations 16-23 may be prepared essentially as described in Preparation 15

| Prep | Compound | Structure | Stereo | MS (m/z) |
|---|---|---|---|---|
| 16 | (3S)-3-[1-(2-trifluoromethyl-3-pyridyloxy)-3-methyl-butyl]-pyrrolidine-1-carboxylic acid tert-butyl ester | 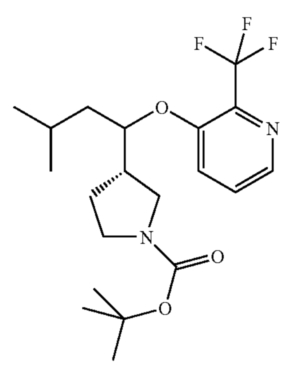 | S-1 | 425 (M + Na) |
| 17 | (3S)-3-[1-(2-trifluoromethyl-3-pyridyloxy)-3-methyl-butyl]-pyrrolidine-1-carboxylic acid tert-butyl ester | 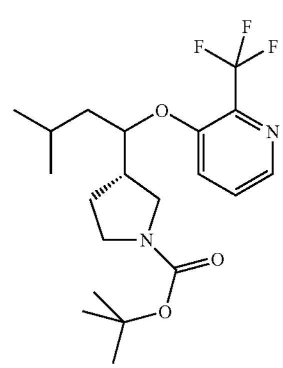 | S-2 | 425 (M + Na) |

-continued

| Prep | Compound | Structure | Stereo | MS (m/z) |
|---|---|---|---|---|
| 18 | (3S)-3-[1-(2-trifluoromethyl-3-pyridyloxy)-1-cyclobutyl-methyl]-pyrrolidine-1-carboxylic acid tert-butyl ester | 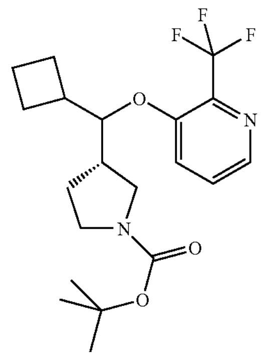 | S-1 | 423.2 (M + 23) |
| 19 | (3S)-3-[1-(2-trifluoromethyl-3-pyridyloxy)-1-cyclobutyl-methyl]-pyrrolidine-1-carboxylic acid tert-butyl ester | 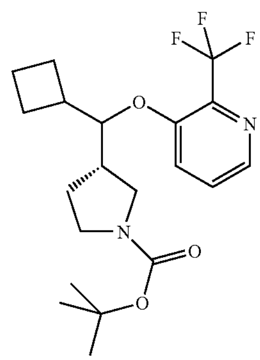 | S-2 | 423.2 (M + 23) |
| 20 | (3S)-3-[1-(6-chloro-2-methyl-3-pyridyloxy)-1-cyclobutyl-methyl]-pyrrolidine-1-carboxylic acid tert-butyl ester | 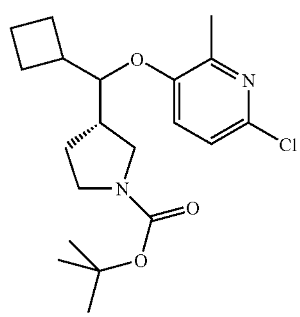 | S-1 | 325.2 (M − 55) |
| 21 | (3S)-3-[1-(6-chloro-2-methyl-3-pyridyloxy)-1-cyclobutyl-methyl]-pyrrolidine-1-carboxylic acid tert-butyl ester | 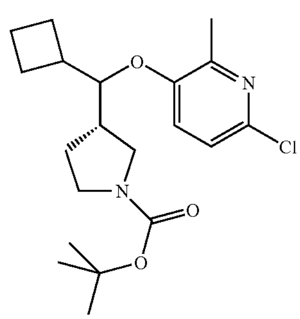 | S-2 | 325.2 (M − 55) |

| Prep | Compound | Structure | Stereo | MS (m/z) |
|------|----------|-----------|--------|----------|
| 22 | 3-[1-(6-chloro-2-methyl-3-pyridyloxy)-2-cyclobutyl-ethyl]-pyrrolidine-1-carboxylic acid tert-butyl ester | 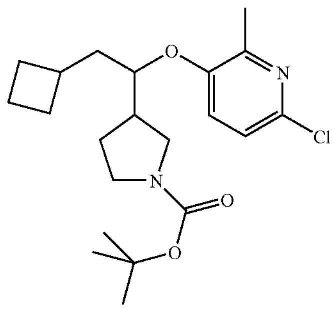 | D-1 | 339.2 (M − 55) |
| 23 | 3-[1-(6-chloro-2-methyl-3-pyridyloxy)-2-cyclobutyl-ethyl]-pyrrolidine-1-carboxylic acid tert-butyl ester | 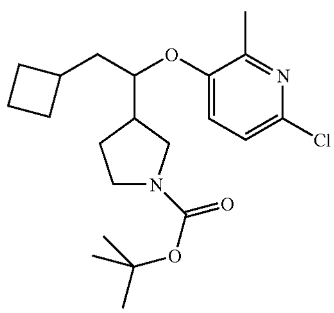 | D-2 | 339.2 (M − 55) |

Preparation 24: 3-[1-(6-Chloro-3-pyridyloxy)-3-methyl-butyl]-pyrrolidine-1-carboxylic acid tert-butyl ester isomer 1 (D2E1) and isomer 2 (D2E2)

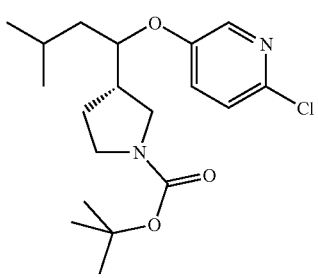

Mitsunobu Reaction

Bubble nitrogen through a solution of 3-(1-hydroxy-3-methyl-butyl)-pyrrolidine-1-carboxylic acid tert-butyl ester (D1) (600 mg, 2.33 mmol) and 2-chloro-5-hydroxy-pyridine (0.451 g, 3.50 mmol) in toluene (10 mL) at room temperature for 10 minutes. Add tri-n-butylphosphine (0.872 mL, 3.50 mmol) followed by azodicarboxylic acid dipiperidide (0.882 g, 3.50 mmol). Heat the reaction mixture to 70° C., and stir over night. Add additional 3-(1-hydroxy-3-methyl-butyl)-pyrrolidine-1-carboxylic acid tert-butyl ester (D1) (600 mg, 2.33 mmol), tri-n-butylphosphine (0.872 mL, 3.50 mmol) and azodicarboxylic acid dipiperidide (0.882 g, 3.50 mmol). Continue to stir at 70° C. for 3 hours. Cool the mixture to room temperature and pour into saturated aqueous NaHCO$_3$. Extract with ethyl acetate (2×), combine the organic extracts, dry (Na$_2$SO$_4$), filter and concentrate. Purify the crude residue by silica gel chromatography eluting with 0-20% ethyl acetate in hexanes to afford 180 mg of 3-[1-(6-chloro-3-pyridyloxy)-3-methyl-butyl]-pyrrolidine-1-carboxylic acid tert-butyl ester (D2) for chiral separation.

Chiral Chromatographic Resolution.

Separate the mixture of isomers of 3-[1-(6-chloro-3-pyridyloxy)-3-methyl-butyl]-pyrrolidine-1-carboxylic acid tert-butyl ester (D2) using super critical fluid chromatography on a OD-H column eluting with 12% isopropylamine/CO$_2$ with 0.2% diethylmethylamine to obtain 3-[1-(6-chloro-3-pyridyloxy)-3-methyl-butyl]-pyrrolidine-1-carboxylic acid tert-butyl ester (D2E1), as the first eluting isomer (80.6 mg, 9.4%) and 3-[1-(6-chloro-3-pyridyloxy)-3-methyl-butyl]-pyrrolidine-1-carboxylic acid tert-butyl ester (D2E2) as the second eluting isomer (81.2 mg, 9.4%). MS (m/z)=391 [M+1].

The compounds of Preparations 25-28 may be prepared essentially as described in Preparation 24.

| Prep | Compound | Structure | Stereo | Separation conditions | MS (m/z) |
|---|---|---|---|---|---|
| 25 | 3-[1-(2-Chloro-4-methyl-3-pyridyloxy)-3-methyl-butyl]-pyrrolidine-1-carboxylic acid tert-butyl ester | 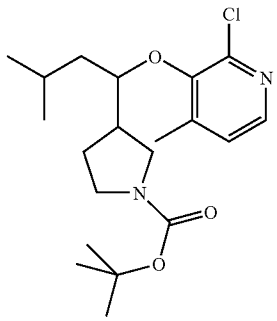 | D2E1 | AD-H, 5% MeOH, 0.2% DEMA | 405 (M + Na) |
| 26 | 3-[1-(2-Chloro-4-methyl-3-pyridyloxy)-3-methyl-butyl]-pyrrolidine-1-carboxylic acid tert-butyl ester | 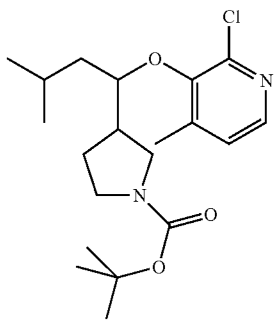 | D2E2 | AD-H, 5% MeOH, 0.2% DEMA | 405 (M + Na) |
| 27 | 3-[1-(2-Methyl-3-pyridyloxy)-3-methyl-butyl]-pyrrolidine-1-carboxylic acid tert-butyl ester | 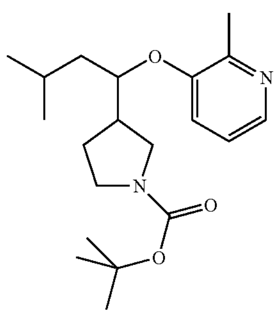 | D2E1 | OD-H, 10% MeOH, 0.2% DEMA | 371 (M + Na) |
| 28 | 3-[1-(2-Methyl-3-pyridyloxy)-3-methyl-butyl]-pyrrolidine-1-carboxylic acid tert-butyl ester | 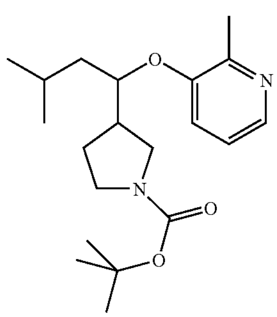 | D2E2 | OD-H, 10% MeOH, 0.2% DEMA | 371 (M + Na) |

Preparation 29: (3S)-3-[1-(6-chloro-2-methyl-3-pyridyloxy)-3-methyl-butyl]-pyrrolidine-1-carboxylic acid tert-butyl ester (S-2)

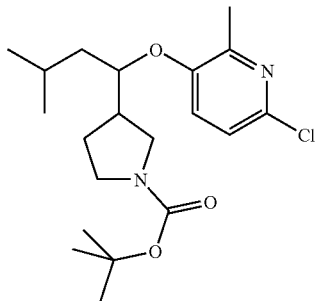

Mix sodium hydride (60%, 121.2 mg, 3.03 mmol), (3S)-3-(1-hydroxy-3-methyl-butyl)-pyrrolidine-1-carboxylic acid tert-butyl ester (S-2) (0.65 g, 2.53 mmol) and DMSO (10.0 mL). Stir the mixture for 1 h at room temperature under an atmosphere of nitrogen Add 2-chloro-5-fluoropicoline (2.21 g, 15.2 mmol)and stir the mixture at 70° C. overnight. Cool the mixture to room temperature, quench the reaction with brine and extract with ethyl acetate. Combine the organic extracts and dry (MgSO₄), filter and concentrate. Purify the crude residue by silica gel chromatography, eluting with 0-20% ethyl acetate in hexane followed by 20% ethyl acetate in hexane to afford 0.58 g (60%) of the title compound. MS (m/z)=425.0 (M+23).

Preparation 30: 6-Methoxy-2-methyl-pyridin-3-ol

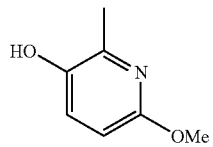

Add hydrogen peroxide (7.69 mL, 89.8 mmol) to a stirred mixture of 2-methoxy-6-methyl-5-pyridylboronic acid (5.0 g, 30 mmol) in dichloromethane (100 mL) kept under nitrogen at room temperature. Stir overnight at ambient temperature, add water and extract the mixture with dichloromethane. Combine the organic phases, dry (MgSO₄), filter and concentrate to afford 2.6 g (62%) of the title compound. MS (m/z)= 140 [M+1]

EXAMPLE 1

(3S)-3-[1-(6-chloro-2-methyl-3-pyridyloxy)-2-cyclopropyl-ethyl]-pyrrolidine, L-tartrate (S-1)

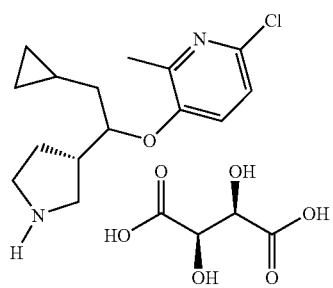

Deprotection

Add trifluoroacetic acid (1.51 g, 1.0 mL, 13.2 mmol) to a solution of (3S)-3-[1-(6-chloro-2-methyl-3-pyridyloxy)-2-cyclopropyl-ethyl]-pyrrolidine-1-carboxylic acid tert-butyl ester (S-1) (99.0 mg, 0.260 mmol) in methoxybenzene (1.0 mL) and dichloromethane (2.0 mL). Stir under nitrogen at room temperature for 1 h. Load the mixture directly onto a pre-packed SCX column and rinse with CH₂Cl₂ followed by CH₃OH. Elute with 2M NH₃ in methanol and concentrate under reduced pressure to give 58 mg (79%) of (3S)-3-[1-(6-chloro-2-methyl-3-pyridyloxy)-2-cyclopropyl-ethyl]-pyrrolidine (S-1). MS (m/z)=281.2 [M+1]

Salt Formation

Add L-tartaric acid (31.0 mg, 0.207 mmol) to a solution of (3S)-3-[1-(6-chloro-2-methyl-3-pyridyloxy)-2-cyclopropyl-ethyl]-pyrrolidine (S-1) (58.0 mg, 0.207 mmol) in methanol (2 mL). Stir the mixture at room temperature for an hour under nitrogen. Concentrate and dry in a vacuum oven to obtain 89.0 mg (99%) of the title compound.
MS (m/z)=281.0 [M+1]

The compounds of EXAMPLES 2-8 may be prepared essentially as described in EXAMPLE 1.

| Ex. | Compound | Structure | Stereo | MS, (m/z) |
|---|---|---|---|---|
| 2 | 3-[1-(2-Chloro-4-methyl-3-pyridyloxy)-3-methyl-butyl]-pyrrolidine, L-tartrate | 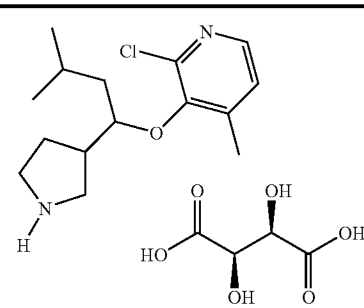 | D2E2 | 283 [M + 1] |

-continued

| Ex. | Compound | Structure | Stereo | MS, (m/z) |
|---|---|---|---|---|
| 3 | 3-[1-(6-Chloro-3-pyridyloxy)-3-methyl-butyl]-pyrrolidine, L-tartrate | 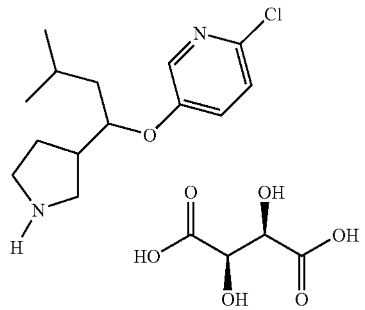 | D2E2 | 269 [M + 1] |
| 4 | (3S)-3-[1-(2-trifluoromethyl-3-pyridyloxy)-3-methyl-butyl]-pyrrolidine, L-tartrate | 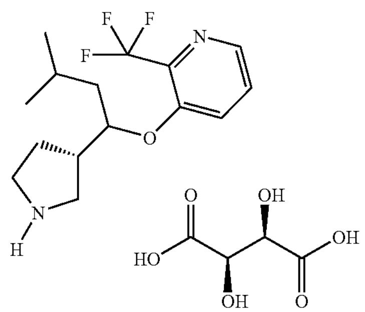 | S-1 | 303 [M + 1] |
| 5 | 3-(3-Methyl-1-(2-methyl-3-pyridyloxy)butyl) pyrrolidine, L-tartrate | 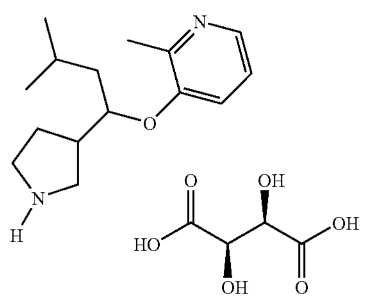 | D2E2 | 249 [M + 1] |
| 6 | (3S)-3-(cyclobutyl(2-(trifluoromethyl)-3-pyridyloxy)methyl) pyrrolidine, L-tartrate | 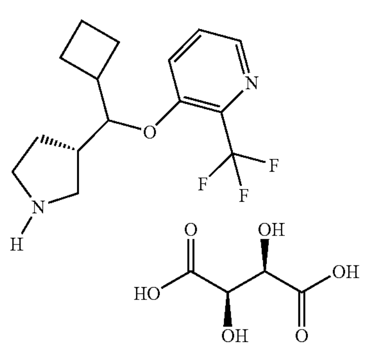 | S-1 | 301 [M + 1] |

-continued

| Ex. | Compound | Structure | Stereo | MS, (m/z) |
|---|---|---|---|---|
| 7 | (3S)-3-(cyclobutyl-(6-chloro-2-methyl-3-pyridyloxy)methyl)pyrrolidine, L-tartrate | 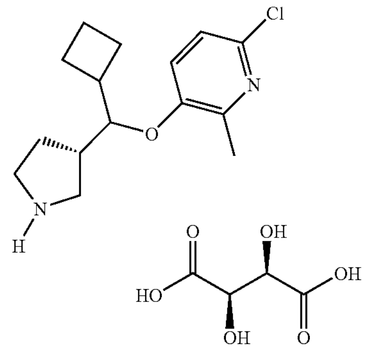 | S-1 | 281.2 [M + 1] |
| 8 | 3-(2-cyclobutyl-1-(6-chloro2-methyl-3-pyridyloxy)-ethyl)pyrrolidine, L-tartrate | 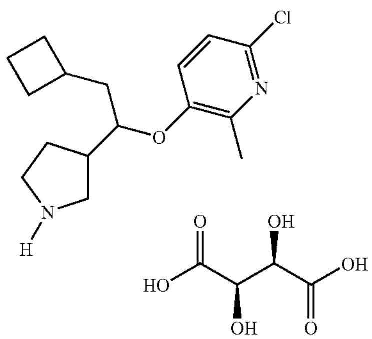 | D1 | 295.0 [M + 1] |

EXAMPLE 9

(3S)-3-(3-Methyl-1-(2-methyl-6-methylamino-3-pyridyloxy)butyl)-pyrrolidine, L-tartrate (S-2)

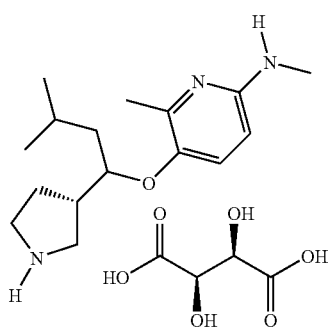

Pd-Catalyzed Coupling Reaction

Charge a 5 mL microwave vessel with 0.294 mL of a 10 mg/mL solution of Pd(OAc)$_2$ (2.93 mg, 0.013 mmol) in toluene. Add 0.756 mL of a 10 mg/mL solution of cataCXium@PtB from Degussa [(N-Phenyl-2-(di-t-butylphosphino)pyrrole] (7.50 mg, 0.026 mmol) in toluene and sodium tert-butoxide (30.2 mg, 0.314 mmol) under an atmosphere of nitrogen. Add 1 mL of a 10 mg/mL solution of (3S)-3-[1-(6-chloro-2-methyl-3-pyridyloxy)-3-methyl-butyl]-pyrrolidine-1-carboxylic acid tert-butyl ester (S-2) (0.100 g, 0.261 mmol) in toluene and methylamine (0.392 mL, 0.785 mmol). Heat the reaction mixture at 150° C. for 1.5 hours. Add Si—SH resin and stir for 2 hours to scavenge the Pd. Pour the crude mixture onto a pre-packed SCX-column washed with methanol, release the product with 2M NH$_3$ in methanol and concentrate. The crude product is used in the next step without further purification. MS (m/z)=378 [M+1]

Deprotection

Stir a mixture of (3S)-3-[1-(2-methyl-6-methylamino-3-pyridyloxy)-3-methyl-butyl]-pyrrolidine-1-carboxylic acid tert-butyl ester (S-2) and aqueous HCl (4M, 0.261 mL, 1.04 mmol) at room temperature for 1 hour. After full conversion, concentrate the mixture, dissolve in dichloromethane and load the mixture onto a pre-packed SCX column. Wash with dichloromethane followed by methanol. Release the product with 2M NH$_3$ in methanol and concentrate under reduced pressure. Purify the crude residue by reverse phase chromatography (17-43% gradient actonitrile in 0.01 M ammoniumformate in water, 85 mL/min, for 8 min., C$^{18}$ ODB XBridge column, 30×75 mm, 5 µm) to give 9 mg (12%) of (3S)-3-[1-(2-methyl-6-methylamino-3-pyridyloxy)-3-methyl-butyl]-pyrrolidine (S-2). MS (m/z)=278 [M+1].

Prepare the L-tartrate salt by dissolving the purified material into a mixture of acetonitrile/methanol (5:1). Add a 1N aqueous solution of L-tartaric acid (1.05 equiv). Lyophilize the mixture to afford the title compound as a solid. MS (m/z)=278 [M+1].

EXAMPLE 10

(3S)-3-[1-(6-cyclopropylamino-2-methyl-3-pyridyloxy)-3-methyl-butyl]-pyrrolidine, L-tartrate (S-2)

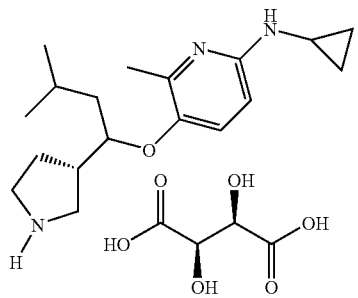

The title compound may be prepared essentially as described in EXAMPLE 9. MS (m/z)=304 [M+1].

EXAMPLE 11

(3S)-3-(1-(6-ethoxy-2-methyl-3-pyridyloxy)-3-methyl-butyl)-pyrrolidine, L-tartrate (S-2)

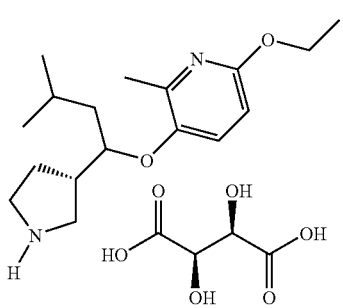

Pd-Catalyzed Coupling Reaction

Charge a 5 mL microwave vessel with (S)-(−)-2,2'-bis(di-p-tolylphosphino)-1,1'-binaphthyl (15.1 mg, 0.0222 mmol), tris(dibenzylideneacetone)dipalladium (0) (10.2 mg, 0.0111 mmol) and toluene (2 mL). Add a solution of (3S)-3-[1-(6-chloro-2-methyl-3-pyridyloxy)-3-methyl-butyl]-pyrrolidine-1-carboxylic acid tert-butyl ester (S-2) (85.0 mg, 0.222 mmol) in toluene (1 mL) followed by sodium ethoxide (0.216 mg, 0.666 mmol). The reaction mixture is irradiated under microwave conditions at 140° C. for 30 minutes. Add Si—SH resin and stir for 2 hours to scavenge the Pd. Pour the crude mixture onto an SCX-column, wash with methanol, release the product with 2M $NH_3$ in methanol and concentrate. The crude product is used in the next step without further purification. MS (m/z)=393 [M+1]

Deprotection

Stir a mixture of (3S)-3-[1-(6-ethoxy-2-methyl-3-pyridyloxy)-3-methyl-butyl]-pyrrolidine-1-carboxylic acid tert-butyl ester (S-2) and aqueous HCl (4N in dioxane, 0.261 mL, 1.04 mmol) at room temperature for 1 hour. After full conversion, concentrate the mixture, dissolve the residue in chloromethane and load onto a pre-packed SCX column. Wash the column with dichloromethane followed by methanol. Release the product with 2M $NH_3$ in methanol and concentrate under reduced pressure. Purify the crude residue by reverse phase chromatography (34-60% gradient actonitrile in 0.01 M ammoniumformate in water, 85 mL/min, for 8 min., $C^{18}$ ODB XBridge column, 30×75 mm, 5 µm) to give 13.4 mg (21%) of (3S)-3-[1-(6-ethoxy-2-methyl-3-pyridyloxy)-3-methyl-butyl]-pyrrolidine (S-2). MS (m/z)=293 [M+1].

Prepare the L-tartrate salt by dissolving the purified material into a mixture of acetonitrile/methanol (5:1). Add a 1N aqueous solution of L-tartaric acid (1.05 equiv). Lyophilize the mixture to afford the title compound as a solid. MS (m/z)=293 [M+1].

EXAMPLE 12

(3S)-3-(1-(6-chloro-2-methyl-3-pyridyloxy)butyl)-pyrrolidine, L-tartrate (S-2)

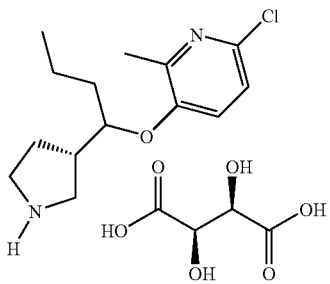

Add (3S)-3-(1-hydroxy-butyl)-pyrrolidine-1-carboxylic acid tert-butyl ester (S-2) (0.400 g, 1.64 mmol) and sodium hydride (60%, 132 mg, 3.29 mmol) to DMSO (10 mL). Keep the mixture under an atmosphere of nitrogen and stir for 15 minutes. Add 6-chloro-3-fluoropicoline (1.44 g, 9.86 mmol). Heat the mixture to 70° C. and stir for 1 hour. Pour the reaction mixture onto brine and extract with EtOAc. Combine the extracts and dry (MgSO4), filter and concentrate. Use the crude residue in the next reaction without further purification.

The deprotection and L-tartrate formation are essentially performed as in EXAMPLE 1 to afford the title compound (384 mg, 56%). MS (m/z)=268 [M+1].

The compounds of EXAMPLES 13-16 may be prepared essentially as described in EXAMPLE 12.

| Ex. | Compound | Structure | Stereo | MS, (m/z) |
|---|---|---|---|---|
| 13 | (3S)-3-[1-(6-Chloro-2-methyl-3-pyridyloxy)-3-methyl-butyl]-pyrrolidine, L-tartrate | 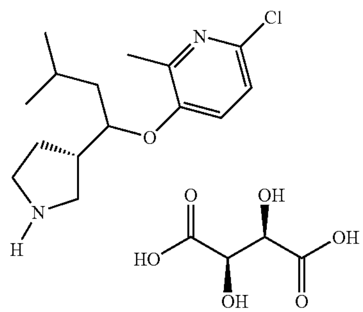 | S-2 | 269 [M + 1] |
| 14 | (3S)-3-[1-(6-Bromo-2-methyl-3-pyridyloxy)-3-methyl-butyl]-pyrrolidine, L-tartrate | 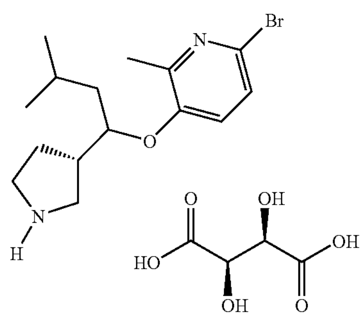 | S-2 | 314 [M + 1] |
| 15 | (3S)-3-[1-(2-Bromo-6-methyl-3-pyridyloxy)-3-methyl-butyl]-pyrrolidine, L-tartrate | 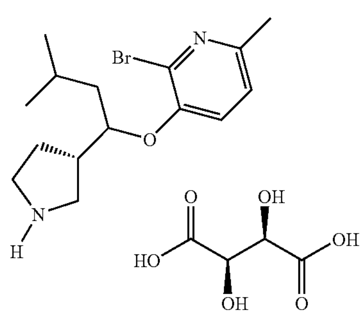 | S-2 | 328 [M + 1] |
| 16 | (3S)-3-[1-(6-Chloro-2-methyl-3-pyridyloxy)-1-cyclopropylmethyl]-pyrrolidine, L-tartrate | 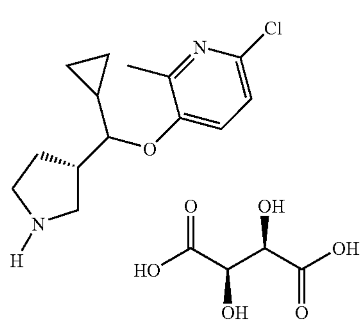 | S-2 | 267 [M + 1] |

EXAMPLE 17

(3S)-3-(1-(6-bromo-3-pyridyloxy)-3-methyl-butyl)-pyrrolidine, L-tartrate (S-2)

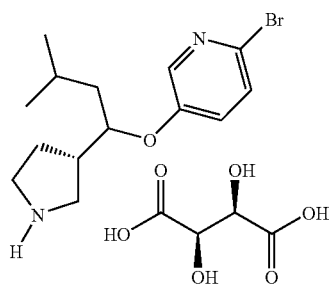

Charge a reaction vessel with a solution of (3S)-3-(1-hydroxy-3-methyl-butyl)-pyrrolidine-1-carboxylic acid tert-butyl ester (S-2) (100 mg, 0.389 mmol) in DMF (3 mL). Add 3-fluoro-6-bromo-3-pyridine (90 mg, 0.051 mmol), 18-crown-6 (10.3 mg, 0.039 mmol) and sodium tert-butoxide (68.2 mg, 0.699 mmol). Heat the reaction at 80° C. for several hours until the LC/MS shows conversion to the desired product. Evaporate the solvent and use the residue in the next reaction without further purification.

The deprotection and the salt formation are essentially performed as in EXAMPLE 11 to afford the title compound. MS (m/z)=314 [M+1].

EXAMPLE 18

(3S)-3-[1-(6-Chloro-3-pyridyloxy)-3-methyl-butyl]-pyrrolidine, L-tartrate (S-2)

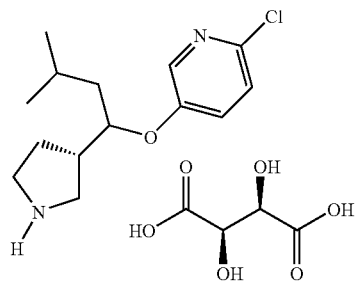

The title compound may be prepared essentially as described in EXAMPLE 17. MS (m/z)=269 [M+1].

EXAMPLE 19

(3S)-3-(1-(6-methoxy-2-methyl-3-pyridyloxy)-3-methyl-butyl)-pyrrolidine, L-tartrate (S-2)

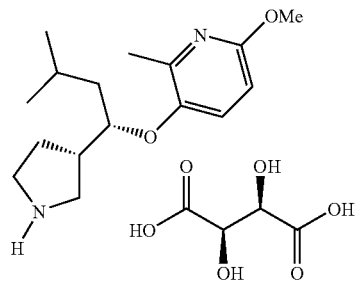

Purge nitrogen through a solution of (3S)-3-(1-hydroxy-3-methyl-butyl)-pyrrolidine-1-carboxylic acid tert-butyl ester (S-1) (0.5 g, 1.94 mmol) and 6-methoxy-2-methyl-pyridin-3-ol (0.41 g, 2.91 mmol) in toluene (10 mL) at room temperature for 10 minutes. Add tri-n-butylphosphine (0.73 mL, 2.91 mmol) followed by azodicarboxylic acid dipiperidide (0.59 mg, 2.91 mmol). Heat the reaction mixture to 70° C., and stir over night. Cool the mixture to room temperature and pour onto saturated aqueous NaHCO$_3$ (50 mL). Extract with ethyl acetate (2×), combine the organic extracts and dry (Na$_2$SO$_4$), filter and concentrate. Purify the crude residue by silica gel chromatography eluting with 0-20% ethyl acetate in hexanes to afford (3S)-3-[1-(6-methoxy-2-methyl-3-pyridyloxy)-3-methyl-butyl]-pyrrolidine-1-carboxylic acid tert-butyl ester (S-2) (101 mg, 13%). The deprotection and the L-tartarte formation are performed essentially as in EXAMPLE 1 to afford the title compound. MS (m/z)=279 [M+1]

EXAMPLE 19A (3S)-3-(1-(6-methoxy-2-methyl-3-pyridyloxy)-3-methyl-butyl)-pyrrolidine, (S-2). Alternative Synthesis

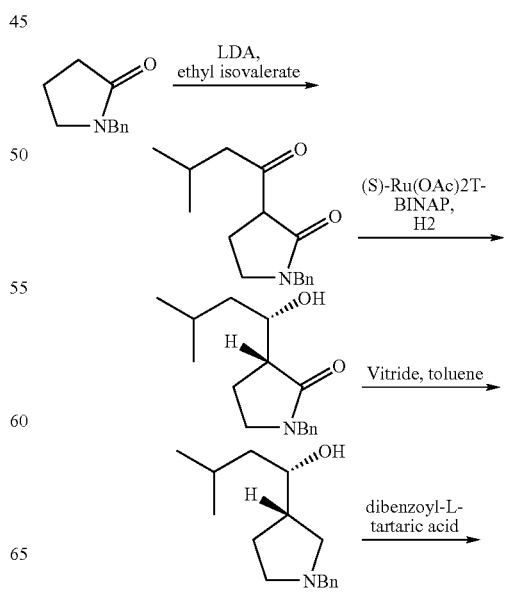

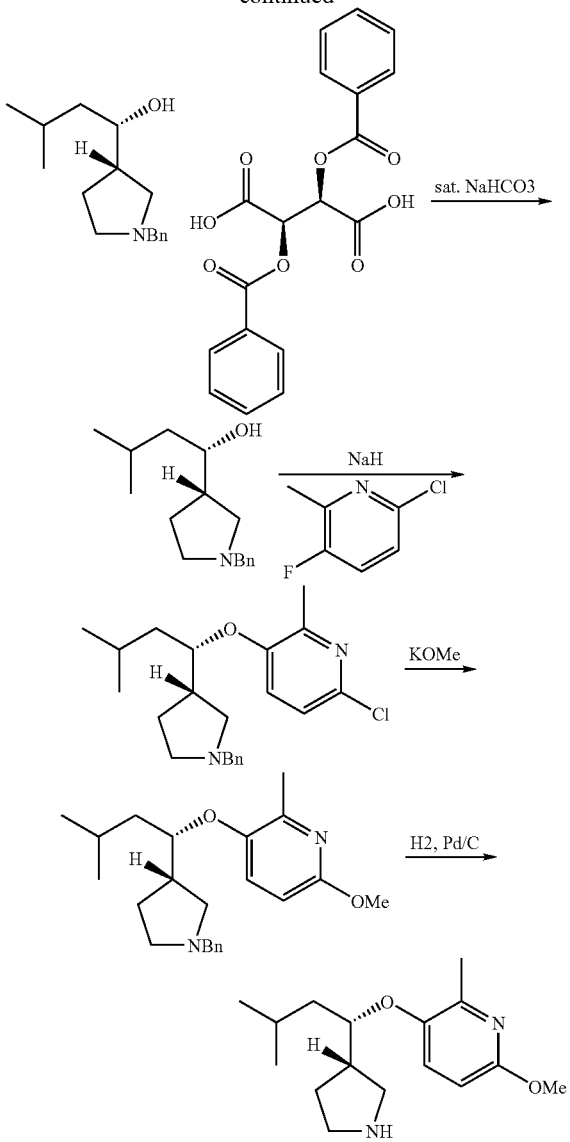

(S)-1-Benzyl-3-(3-methylbutanoyl)pyrrolidin-2-one

Charge a 5 L, 3-neck round bottom flask equipped with a magnetic stirrer, thermal couple, addition funnel and $N_2$ inlet with diisopropylamine (176 mL, 1265 mmoles) and 2-methyltetrahydrofuran (500 mL). Cool the solution to ~−10° C. (salt/ice bath) with stirring and add a solution of n-BuLi (2.5 M in hexanes, 504 mL, 1259 mmoles) drop wise while maintaining a temperature at or below 0° C. Rinse the addition funnel with 2-methyltetrahydrofuran (25 mL). Stir the solution for about 15 min, at ~−5° C. Add a solution of N-benzyl-2-pyrrolidinone (100.8 g, 575 2 mmoles), ethyl isovalerate (90 g, 690 mmoles) in 2-Me-THF (500 mL) drop wise at a rate to maintain a temperature at or below 5° C. to provide a yellow slurry. Stir the reaction mixture about 1 hour at −5° C., add heptane (1 L) drop wise, and stir for an additional 1 hr. at −5° C. Collect the solid by filtration through a medium fritted funnel, wash with a 1:1 solution of 2-methyltetrahydrofuran/heptane (250 mL) followed by heptane (250 mL) and air dry until the solid becomes powder-like. Place the yellow solid into a 5 L, 3-neck round bottom flask equipped with a magnetic stirrer and add MTBE (1 L) and 10% citric acid (1 L). Stir the mixture for about 1 hour at room temperature to provide a homogeneous mixture. Separate the layers and wash the organic layer with $H_2O$ (2×500 mL), followed by brine (500 mL). Dry over $Na_2SO_4$, filter and concentrate to give the crude intermediate (128 g) as an orange oil. A Kuegelrohr distillation removes the major impurity from the crude material to yield the desired intermediate as a dark orange oil (117.4 g, 452.7 mmoles, 78.7% yield). $^1$H NMR (300 MHz, $CDCl_3$) δ 7.38-7.16 (m, 5H), 4.55-4.35 (m, 2H), 3.62 (dd, 1H, J=5.86, 9.37 Hz), 3.38-3.14 (m, 2H), 2.92-2.8 (m, 1H), 2.64-2.42 (m, 2H), 2.28-2.11 (m, 1H), 2.08-1.93 (m, 1H), 0.96 (d, 3H, J=7.03 Hz) 0.93 (d, 3H, J=7.04 Hz). GC/MS=260 (M+1).

(R)-1-Benzyl-3-((S)-1-hydroxy-3-methylbutyl)pyrrolidin-2-one

Charge a 400 mL stainless steel autoclave vessel with a solution of (S)-1-benzyl-3-(3-methylbutanoyl)pyrrolidin-2-one (20 g, 77.12 mmoles) in IPA (250 mL), followed by 35% HCl (6% compared to the substrate, 4.63 mmoles, M=36.4 g/mol, d=1.18 g/mL, 0.408 mL). Purged with $N_2$ gas (5x~50 PSI). Vent the vessel and quickly add (S)-Ru(OAc)$_2$T-BINAP (250 mg, 0.2784 mmoles), while a stream of $N_2$ flows over the top of the reaction mixture Immediately seal the autoclave and purge with $N_2$ gas (5x~50 PSI). Purge the vessel with $H_2$ gas (5×60 PSI) and then charge of the vessel with $H_2$ gas (60 PSI). Stir the reaction mixture at 65° C. overnight (~16-18 hours). The pressure of the vessel increases to ~70 PSI during this time and the vessel is refilled with $H_2$ gas as needed and not kept at a constant pressure of 60 PSI over the course of the reaction. Cool to room temperature and concentrate under reduced pressure to give crude (R)-1-benzyl-3-((S)-1-hydroxy-3-methylbutyl)pyrrolidin-2-one as a dark brown oil that was taken onto the next step without further purification (21.6 g, 82.6 mmoles, ~95-97% ee, >100% yield). $^1$H NMR (300 MHz, $CDCl_3$) δ 7.38-7.18 (m, 5H), 4.48 (s, 2H), 4.34-4.22 (m, 1H), 3.28-3.14 (m, 2H), 2.63 (td, 1H, J=2.93, 9.37 Hz), 2.47 (d, 1H, J=5.86 Hz), 2.12-1.70 (m, 3H), 1.54-1.38 (m, 1H), 1.24-1.10 (m, 1H), 0.95 (d, 3H, J=3.51 Hz), 0.93 (d, 3H, J=2.93 Hz). GC/MS=262 (M+1).

(S)-1-Benzyl-3-((S)-1-hydroxy-3-methylbutyl)-pyrrolidine

Charge a 1 L, 3-neck round bottom flask equipped with a magnetic stirrer, thermal couple, addition funnel and $N_2$ inlet with crude (R)-1-benzyl-3-((S)-1-hydroxy-3-methylbutyl)pyrrolidin-2-one (38.26 mmoles, assumed) and toluene (100 mL). Cool the slightly heterogeneous stirring solution to 0° C. (salt/ice bath) and add a solution of Vitride™ (Rohm & Haas) (65 wt % in toluene, 24 mL, 86.085 mmoles) and toluene (70 mL) drop wise while maintaining a temperature at or below 5° C. Rinse the addition funnel with toluene (10-20 mL). Stir at room temperature overnight (~16 hr). Cool the reaction mixture to 0° C. (salt/ice bath) and quenched with saturated Rochell's salt solution (200 mL) followed by MTBE (200 mL). Allow the mixture to warm to room temperature with stirring and then stir at this temperature for 1 hour. Separate the organic and aqueous layers and wash the organic layer with $H_2O$ (2×200 mL), then brine (200 mL), and then dry over $Na_2SO_4$. Filter and concentrate to give the desired intermediate as a brown oil (9.61 g, 38.85 mmoles, >100% yield). $^1$H NMR (300 MHz, $CDCl_3$) δ 7.36-7.18 (m, 5H), 3.82-3.72 (m, 1H), 3.58 (dd, 2H, 7.61, 20.51 Hz), 2.87 (td, 1H, J=4.10, 8.79

Hz), 2.79-2.70 (m, 1H), 2.48-2.38 (m, 1H), 2.26-2.04 (m, 2H), 1.98-1.64 (m, 3H), 1.46-1.32 (m, 1H), 1.14-0.98 (m, 1H), 0.92 (d, 3H, J=1.18 Hz), 0.89 (d, 3H, J=1.76 Hz). LC/MS=248.1 (M+1).

Resolution/Purification of (S)-1-benzyl-3-((S)-1-hydroxy-3-methylbutyl)-pyrrolidine Charge a 500 mL round bottom flask equipped with a magnetic stir bar and $N_2$ inlet with crude (S)-1-benzyl-3-((S)-1-hydroxy-3-methylbutyl)-pyrrolidine (9.61g, 38.26 mmoles) and MeOAc (96 mL). Add dibenzoyl-(L)-tartaric acid (13.71 g, 38.26 mmoles) in one portion with stirring and allow the reaction mixture to stir at room temperature until the mixture becomes cloudy (~5 min.). Heat in a preheated oil bath at 50° C. overnight with stirring (~16 hours). Cool the reaction mixture to room temperature and isolate the solid by filtration through a medium fritted funnel Wash the solid with methyl acetate (5×20 mL) and allow to air dry to give (S)-1-benzyl-3-((S)-1-hydroxy-3-methylbutyl)-pyrrolidine salt as a white solid (15.1 g, 24.93 mmoles, 65.2% yield over 3 steps, 81.4% isomer recovery assuming 80% ee). LC/MS=248.1 (M+1).

Desalting of (S)-1-benzyl-3-((S)-1-hydroxy-3-methylbutyl)-pyrrolidine salt

Charge a 500 mL round bottom flask equipped with a magnetic stir bar with (S)-1-benzyl-3-((S)-1-hydroxy-3-methylbutyl)-pyrrolidine salt (13.71 g, 22.636 mmoles) and MTBE (140 mL). Add aqueous saturated $NaHCO_3$ (140 mL) and stir the heterogeous mixture at room temperature overnight. Dilute the cloudy solution with EtOAc (140 mL) and aqueous saturated $NaHCO_3$ (50 mL), followed by $H_2O$ (~100 mL), to provide a clear mixture. Separate the layers and dry the organic layer over $Na_2SO_4$. Filter and concentrate to give (S)-1-benzyl-3-((S)-1-hydroxy-3-methylbutyl)-pyrrolidine as a tan oil that was taken onto the next step without further purification (5.37 g, 21.707 mmoles, 95.9% recovery).$^1$H NMR (300 MHz, CDCl$_3$) δ 7.36-7.18 (m, 5H), 3.82-3.72 (m, 1H), 3.58 (dd, 2H, 7.61, 20.51 Hz), 2.87 (td, 1H, J=4.10, 8.79 Hz), 2.79-2.70 (m, 1H), 2.48-2.38 (m, 1H), 2.26-2.04 (m, 2H), 1.98-1.64 (m, 3H), 1.46-1.32 (m, 1H), 1.14-0.98 (m, 1H), 0.92 (d, 3H, J=1.18 Hz), 0.89 (d, 3H, J=1.76 Hz). LC/MS=248.1 (M+1).

(S)-1-benzyl-3-((S)-1-(6-chloro-2-methyl-3-pyridyloxy)-3-methylbutyl)-pyrrolidine Charge a 200 mL round bottom flask equipped with a Claisen adaptor, thermal couple and $N_2$ inlet with (S)-1-benzyl-3-((S)-1-hydroxy-3-methylbutyl)-pyrrolidine (5.69 g, 23 mmoles) and DMA (58 mL). Add NaH (1.29 g, 32.2 mmoles) in one portion with stirring and stir at room temperature for 1 hour. Add 6-chloro-3-fluoro-2-methylpyridine (3.52 g, 24.15 mmoles) in one portion with stirring and then stir at room temperature for 24 hours. Quench the reaction mixture with $H_2O$ (120 mL) and extract with MTBE (120 mL). Wash the organic layer with $H_2O$ (2×60 mL), followed by brine (60 mL), and then dry over $Na_2SO_4$. Filter, concentrate, and then purify the crude material (in toluene) by loading onto silica (225 g, wet with toluene) and eluting with the following: hexanes (2×500 mL), 15% MTBE/hexanes (16×500 mL), 50% MTBE/hexanes (8×500 mL). Concentrate the appropriate fractions to give (S)-1-benzyl-3-((S)-1-(6-chloro-2-methyl-3-pyridyloxy)-3-methylbutyl)-pyrrolidine as a light yellow oil (5.77 g, 15.47 mmoles, 67% yield, purity >98%). $^1$H NMR (300 MHz, CDCl$_3$) δ 7.38-7.20 (m, 5H), 7.06 (s, 2H), 4.32-4.20 (m, 1H), 3.68-3.48 (m, 2H) 2.78-2.64 (m, 2H), 2.64-2.30 (m, 2H), 2.42 (s, 3H), 2.28-2.20 (m, 1H), 2.05-1.85 (m, 1H), 1.82-1.52 (m, 4H), 1.48-1.34 (m, 1H), 0.92 (d, 3H, J=6.45 Hz), 0.88 (d, 3H, J=6.45 Hz). LC/MS=373.2 (M), 375.3 (M+2).

(S)-1-benzyl-3-((S)-1-(6-methoxy-2-methyl-3-pyridyloxy)-3-methylbutyl)-pyrrolidine To a 200 mL RB flask equipped with a magnetic stir bar and $N_2$ inlet was charged with (S)-1-benzyl-3-((S)-1-(6-chloro-2-methyl-3-pyridyloxy)-3-methylbutyl)-pyrrolidine (5.46 g, 14.65 mmoles) and DMSO (30 mL). Add potassium methoxide (4.11 g, 58.61 mmoles) in one portion with stirring. Stir the reaction mixture in an oil bath at 100° C. for 1 hour. Dilute with $H_2O$ (60 mL) and MTBE (60 mL). Separate the layers and wash organic layer with $H_2O$ (2×30 mL), followed by brine (30 mL), and then dry over $Na_2SO_4$. Filter and concentrate the crude material (in toluene). Load onto silica (225 g, wet with toluene), and elute with the following: hexanes (2×500 mL), 50% MTBE/hexanes (6×500 mL). Concentrate the appropriate fractions to give (S)-1-benzyl-3-((S)-1-(6-methoxy-2-methyl-3-pyridyloxy)-3-methylbutyl)-pyrrolidine. (4.32 g, 11.72 mmoles, 80% yield) as a yellow/orange oil. $^1$H NMR (300 MHz, CDCl$_3$) δ 7.34-7.2 (m, 5H), 7.10 (d, 1H, J=8.79 Hz), 6.49 (d, 1H, J=8.79), 4.17-4.07 (m, 1H), 3.88 (s, 3H), 3.68-3.50 (m, 2H), 2.78-2.67 (m, 2H), 2.61-2.48 (m, 1H), 2.48-2.38 (m, 1H), 2.37 (s, 3H), 2.33-2.24 (m, 1H), 2.00-1.50 (m, 5H), 1.44-1.30 (m, 1H), 0.885 (at, 6H, $J_a$=7.03 Hz, $J_b$=6.44 Hz). LC/MS=369.3 (M+1).

(S)-3-((S)-1-(6-methoxy-2-methyl-3-pyridyloxy)-3-methylbutyl)-pyrrolidine

Charge a 400 mL stainless steel autoclave with 20% by weight Pd/C (10%, wet, 820 mg) followed by a solution of (S)-1-benzyl-3-((S)-1-(6-methoxy-2-methyl-3-pyridyloxy)-3-methylbutyl)-pyrrolidine (4.1 g, 11.126 mmoles) in ethanol (82 mL). Purge with $H_2$ gas (3×50 PSI), then charge the vessel with $H_2$ gas (50 PSI). Heat the reaction mixture to 60° C.[1] and stir at 60° C. for 24 hours. The pressure of the vessel increases to ~55 PSI at 60° C. and the vessel is refilled with $H_2$ gas as needed. Allow the reaction mixture to cool to room temperature, filter through a medium fritted funnel charged with celite (wet with ethanol), and wash with ethanol (~80 mL). Concentrate under reduced pressure to give (S)-3-((S)-1-(6-methoxy-2-methyl-3-pyridyloxy)-3-methylbutyl)-pyrrolidine as a light yellow oil (3.02 g, 10.848 mmoles, 97.5% yield). $^1$H NMR (300 MHz, CDCl$_3$) δ 7.12 (d, 1H, J=8.79 Hz), 6.50 (d, 1H, 8.79 Hz), 4.2 (aq, 1H, $J_a$=7.03 Hz, $J_b$=5.27 Hz), 3.87 (s, 3H), 3.08-2.94 (m, 2H), 2.94-2.82 (m, 1H), 2.82-2.70 (m, 1H), 2.50-2.26 (m, 3H), 2.36 (s, 3H), 1.94-1.78 (m, 1H), 1.78-1.52 (m, 3H), 1.44-1.30 (m, 1H), 0.898 (at, 6H, $J_a$=6.45 Hz, $J_b$=7.03 Hz). LC/MS=279.3 (M+1).

EXAMPLE 19B (S)-3-((S)-1-(6-methoxy-2-methyl-3-pyridyloxy)-3-methyl-butyl)-pyrrolidine, D-tartrate

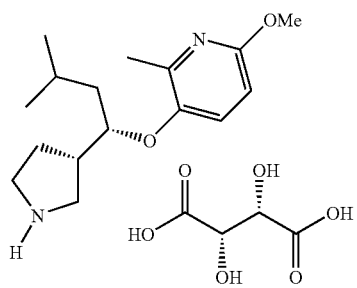

Dissolve (S)-3-((S)-1-(6-methoxy-2-methyl-3-pyridyloxy)-3-methyl-butyl)-pyrrolidine (353 mg) is dissolved in THF (1 mL) at 60° C. while stirring at 1000 rpm. A slightly cloudy yellow solution results. Slowly add a solution of D-tartaric acid (218 mg dissolved in 3 mL THF at 80° C.) to the solution. Filter the solution through a 0.45 μm PTFE syringe filter and add acetonitrile (4 mL). Allow to evaporate, lidless, in a hood. A large amount of off-white solid precipitates after about 20 min. vacuum filter the solution and dry the solids in a 60° C. vacuum oven for 1 hr. to obtain a powdery off-white solid.

X-Ray Powder Diffraction

The XRD pattern of the crystalline is obtained on a Bruker D8 Advance X-ray powder diffractometer, equipped with a CuKα source λ=1.54056 Å) and a Vantec detector, operating at 50 kV and 40 mA. The sample is scanned between 4 and 40° in 2θ, with a step size of 0.02° in 2θ and a scan rate of 9.0 seconds/step, and with 1 mm divergence and receiving slits and a 0.1 mm detector slit. The dry powder is packed into recessed top-loading sample holder and a smooth surface is obtained using a glass slide. The crystal form diffraction patterns are collected at ambient temperature and relative humidity. The background is removed prior to peak picking. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.1 in 2θ will take into account these potential variations without hindering the unequivocal identification of the indicated crystal form. Confirmation of a crystal form may be made based on any unique combination of distinguishing peaks (in units of ° 2θ), typically the more prominent peaks. Thus, a prepared sample of the d-tartrate salt of (3S)-3-(1-(6-methoxy-2-methyl-3-pyridyloxy)-3-methyl-butyl)-pyrrolidine is characterized by an XRD pattern using CuKα radiation as having diffraction peaks (2-theta values) as described in Table 1 below, and in particular having peaks at 4.63 in combination with one or more of the peaks selected from the group consisting of 9.26, 16.12, and 16.59; with a tolerance for the diffraction angles of 0.1 degrees.

TABLE 1

X-ray powder diffraction peaks of the d-tartrate salt of (3S)-3-(1-(6-methoxy-2-methyl-3-pyridyloxy)-3-methyl-butyl)-pyrrolidine.

| Angle 2-Theta ° | d value Angstrom | Intensity % % |
|---|---|---|
| 4.63 | 19.06 | 100 |
| 9.26 | 9.55 | 20 |
| 12.22 | 7.23 | 19 |
| 13.87 | 6.38 | 14 |
| 16.12 | 5.49 | 86 |
| 16.59 | 5.34 | 38 |
| 17.85 | 4.96 | 12 |
| 18.55 | 4.78 | 20 |
| 18.88 | 4.70 | 21 |
| 20.21 | 4.39 | 18 |
| 21.56 | 4.12 | 11 |
| 22.45 | 3.96 | 15 |
| 23.23 | 3.83 | 23 |
| 24.11 | 3.69 | 17 |
| 24.55 | 3.62 | 12 |
| 25.63 | 3.47 | 12 |
| 26.48 | 3.36 | 15 |
| 26.64 | 3.34 | 10 |

The compounds of EXAMPLES 20-32 may be prepared essentially as described in EXAMPLE 19.

| Ex. | Compound | Structure | Stereo | MS, (m/z) |
|---|---|---|---|---|
| 20 | (3S)-3-[1-(2-Chloro-3-pyridyloxy)-3-methyl-butyl]-pyrrolidine, L-tartrate | 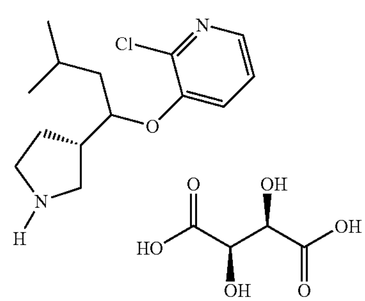 | S-2 | 269 [M + 1] |

| Ex. | Compound | Structure | Stereo | MS, (m/z) |
|---|---|---|---|---|
| 21 | (3S)-3-[1-(2,6-Dimethyl-3-pyridyloxy)-3-methyl-butyl]-pyrrolidine, L-tartrate | 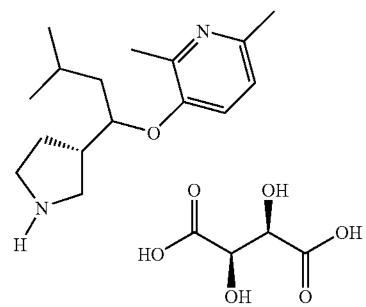 | S-2 | 263 [M + 1] |
| 22 | (3S)-3-[1-(6-Methoxy-3-pyridyloxy)-3-methyl-butyl]-pyrrolidine, L-tartrate | 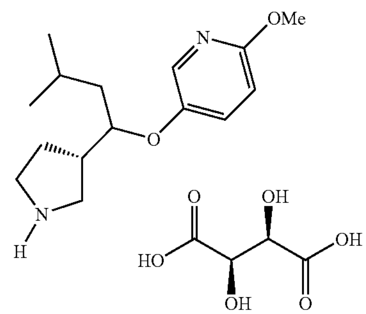 | S-2 | 265 [M + 1] |
| 23 | (3S)-3-[1-(6-Methyl-3-pyridyloxy)-3-methyl-butyl]-pyrrolidine, L-tartrate | 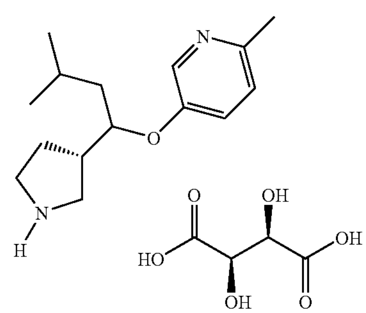 | S-2 | 249 [M + 1] |
| 24 | (3S)-3-[1-(2-Chloro-6-methyl-3-pyridyloxy)-3-methyl-butyl]-pyrrolidine, L-tartrate | 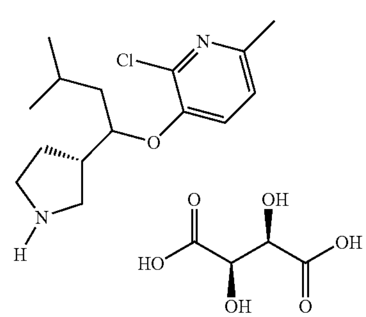 | S-2 | 283 [M + 1] |
| 25 | (3S)-3-[1-(6-Chloro-4-methyl-3-pyridyloxy)-3-methyl-butyl]-pyrrolidine, L-tartrate | 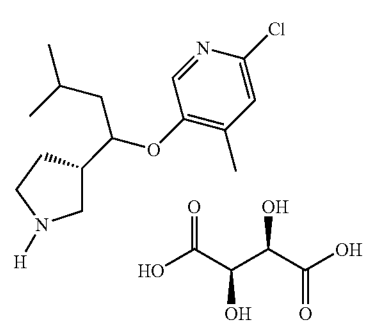 | S-2 | 283 [M + 1] |

-continued
| Ex. | Compound | Structure | Stereo | MS, (m/z) |
|---|---|---|---|---|
| 26 | (3S)-3-[1-(2-Ethyl-6-methyl-3-pyridyloxy)-3-methyl-butyl]-pyrrolidine, L-tartrate | 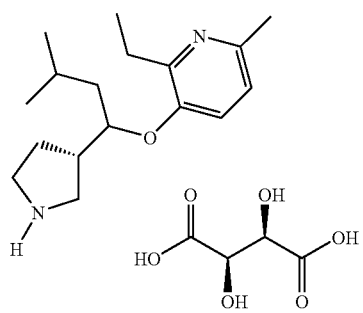 | S-2 | 277 [M + 1] |
| 27 | (3S)-3-[1-(2-Fluoro-6-methyl-3-pyridyloxy)-3-methyl-butyl]-pyrrolidine, L-tartrate | 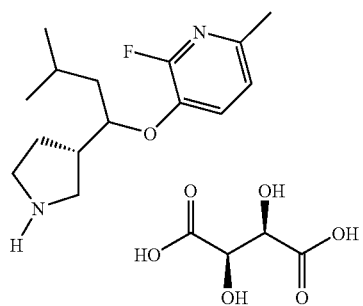 | S-2 | 267 [M + 1] |
| 28 | (3S)-3-[1-(2-Methoxy-6-methyl-3-pyridyloxy)-3-methyl-butyl]-pyrrolidine, L-tartrate | 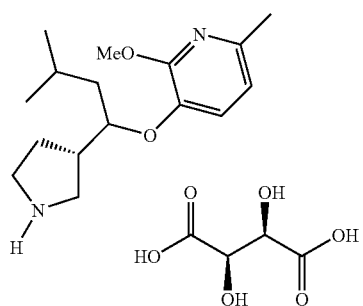 | S-2 | 279 [M + 1] |
| 29 | (3S)-3-[1-(2,6-Dichloro-3-pyridyloxy)-3-methyl-butyl]-pyrrolidine, L-tartrate | 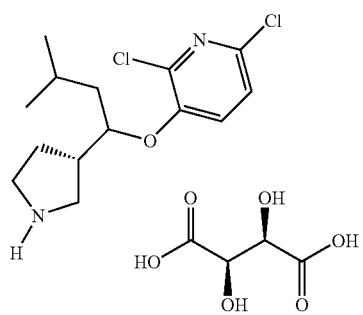 | S-2 | 303 [M + 1] |

-continued

| Ex. | Compound | Structure | Stereo | MS, (m/z) |
|---|---|---|---|---|
| 30 | (3S)-3-[1-(2-Tert-butylcarbonylamino-3-pyridyloxy)-3-methyl-butyl]-pyrrolidine, L-tartrate | 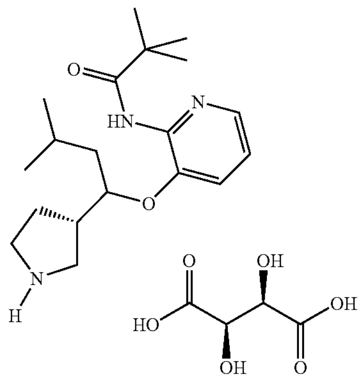 | S-2 | 334 [M + 1] |
| 31 | (3S)-3-[1-(2-Ethoxy-3-pyridyloxy)-3-methyl-butyl]-pyrrolidine, L-tartrate | 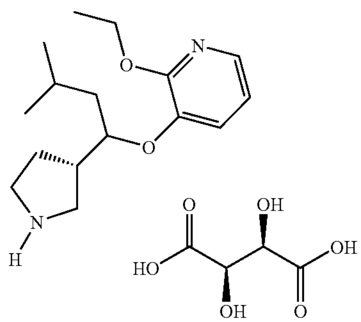 | S-2 | 279 [M + 1] |
| 32 | (3S)-3-[1-(2-cyclopropylmethyloxy-3-pyridyloxy)-3-methyl-butyl]-pyrrolidine, L-tartrate | 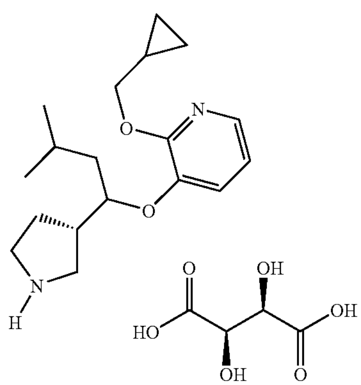 | S-2 | 305 [M + 1] |

EXAMPLE 33

3-(1-(6-chloro-2-methyl-3-pyridyloxy)-2-cyclobutyl-ethyl)-pyrrolidine, L-tartrate (D1E2)

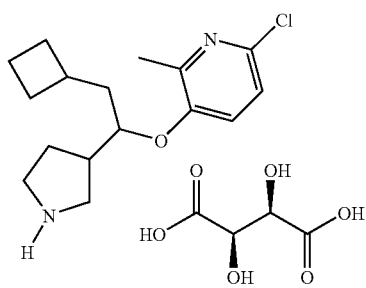

De-Salting

Pour 3-(1-(6-chloro-2-methyl-3-pyridyloxy)-2-cyclobutyl-ethyl)-pyrrolidine, L-tartrate (D1) (80.0 mg, 0.180 mmol) onto an SCX column and rinse with dichloromethane, 50% dichloromethane in methanol and methanol. Elute the compound with 2M NH$_3$ in methanol and concentrate to afford 3-(1-(6-chloro-2-methyl-3-pyridyloxy)-2-cyclobutyl-ethyl)-pyrrolidine (50 mg).

Chiral Chromatographic Resolution

Subject the amine (50 mg) to supercritical fluid chiral chromatography (Chiracel OD-H) eluting with 25% methanol/0.2%isopropylamine/CO2 to afford of 3-(1-(6-chloro-2-methyl-3-pyridyloxy)-2-cyclobutyl-ethyl)-pyrrolidine (D1E1) (21 mg, 40%, >99%ee) and 3-(1-(6-chloro-2-methyl-3-pyridyloxy)-2-cyclobutyl-ethyl)-pyrrolidine (D1E2) (20 mg, 38%, >99 ee).

The L-tartarte formation of 3-(1-(6-chloro-2-methyl-3-pyridyloxy)-2-cyclobutyl-ethyl)-pyrrolidine (D1E2) is essentially performed as in EXAMPLE 1 to afford the title compound. MS (m/z)=295.2 (M+1)

EXAMPLE 34

(3S)-3-(1-(6-Methoxy-2-methyl-3-pyridyloxy)-butyl)-pyrrolidine, L-tartrate (S-2).

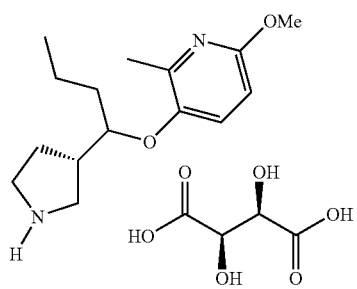

De-Salting

Dissolve the L-tartrate salt of (3S)-3-(1-(6-chloro-2-methyl-3-pyridyloxy)-butyl)-pyrrolidine (S-2) (1.00 g, 2.39 mmol) in methanol and pour the solution onto a SCX column. Rinse the column with methanol and then elute the free amine with 2M NH₃ in methanol. Evaporate the solvent and dry the amine under vacuum to yield 0.65 g (99%) of (3S)-3-(1-(6-chloro-2-methyl-3-pyridyloxy)-butyl)-pyrrolidine (S-2) which was used in the next step without further purification.

Chloride to Methoxy Displacement

Add (3S)-3-(1-(6-chloro-2-methyl-3-pyridyloxy)-butyl)-pyrrolidine (S-2) (0.65 g, 2.44 mmol), DMSO (9.75 mL), methanol (0.493 mL, 12.18 mmol), and sodium hydride (0.390 g, 9.75 mmol) to a reaction vial. Evacuate the vial and purge with nitrogen. Heat the mixture at 100° C. over night. Pour the reaction mixture onto an SCX column and rinse with methanol. Attach the SCX column on top of a silica gel column and elute with 5-30% of NH3OH/ethanol (1:9) in chloroform to obtain 0.420 g (65%) of (3S)-3-(1-(6-methoxy-2-methyl-3-pyridyloxy)-butyl)-pyrrolidine The L-tartarte formation of (3S)-3-(1-(6-methoxy-2-methyl-3-pyridyloxy)-butyl)-pyrrolidine (S-2) is essentially performed as in EXAMPLE 1 to afford the title compound. MS (m/z)=265 [M+1]

EXAMPLE 35

(3S)-3-[1-Cyclobutyl-1-(6-methoxy-2-methyl-3-pyridyloxy)-methyl]-pyrrolidine (S-1), L-tartrate

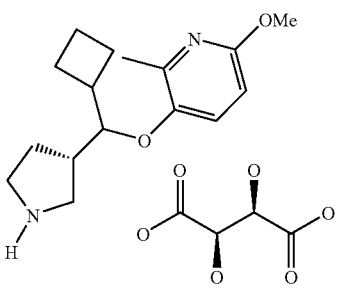

The title compound may be prepared from (3S)-3-[1-cyclobutyl-1-(6-chloro-2-methyl-3-pyridyloxy)-methyl]-pyrrolidine (S-1), L-tartrate essentially as described in EXAMPLE 34. MS (m/z)=277 [M+1]

EXAMPLE 36

(3S)-3-[1-(6-Methoxy-2-methyl-3-pyridyloxy)-2-cyclopropyl-ethyl]-pyrrolidine, L-tartrate (S-1)

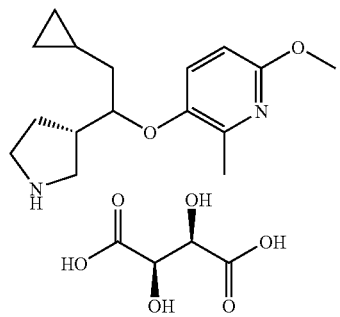

Deprotection

Mix (3S)-3-[1-(6-chloro-2-methyl-3-pyridyloxy)-2-cyclopropyl-ethyl]-pyrrolidine-1-carboxylic acid tert-butyl ester (S-1) (0.50 g, 1.31 mmol), methoxybenzene (6.6 mL) and dichloromethane (6.6 mL) in a reaction vial. Evacuate the vial and purge with nitrogen. Add trifluoroacetic acid (1.51 g, 1.0 mL, 13.2 mmol) and stir the mixture at room temperature for 1 h. Load the mixture directly onto a pre-packed SCX column and rinse with CH₂Cl₂ followed by CH₃OH. Elute with 2M NH₃ in methanol and concentrate under reduced pressure to give 0.353 g (96%) of (3S)-3-[1-(6-chloro-2-methyl-3-pyridyloxy)-2-cyclopropyl-ethyl]-pyrrolidine (S-1). MS (m/z)=281.2 [M+1].

Chloride to Methoxy Displacement

Add (3S)-3-(1-(6-chloro-2-methyl-3-pyridyloxy)-cyclopropyl-ethyl)-pyrrolidine (S-1) (0.35 g, 1.25 mmol), DMSO (4.99 mL), methanol (0.404 mL, 9.97 mmol), and sodium hydride (0.349 g, 8.73 mmol) to a reaction vial. Evacuate the vial and purge with nitrogen. Heat the mixture at 110° C. for 4 h. Dissolve the reaction in a pH 7 buffer and neutralize with 5N HCl. Pour the mixture onto an SCX column and rinse with methanol. Attach the SCX column on top of a silica gel column and elute with 5-35% of NH₄OH/ethanol (1:9) in chloroform to obtain 0.209 g (61%) of (3S)-3-(1-(6-methoxy-2-methyl-3-pyridyloxy)-2-cyclopropyl-ethyl)-pyrrolidine (S-1). MS (m/z)=277 [M+1].

The L-tartarte formation of (3S)-3-(1-(6-methoxy-2-methyl-3-pyridyloxy)-cyclopropyl-ethyl)-pyrrolidine (S-1) is essentially performed as in EXAMPLE 1 to afford the title compound. MS (m/z)=277 [M+1]

EXAMPLE 37

(3S)-3-[1-(6-Chloro-2-methyl-3-pyridyloxy)-2-cyclopropyl-ethyl]-pyrrolidine, L-tartrate (S-1)

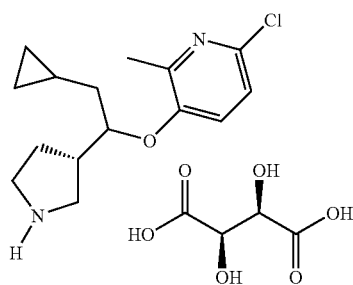

Preparation of Weinreb Amide

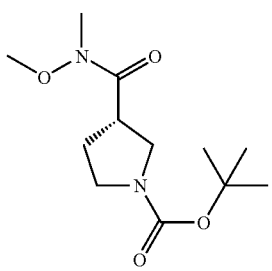

Add a solution of (S)-N-tert-butoxycarbonylpyrrolidine-3-carboxylic acid (40 g, 186 mmol) in THF (240 mL) dropwise to a stirred solution of 1,1'-carbonyldiimidazole (31.4 g, 190 mmol) in THF (160 mL) and stir at room temperature under nitrogen for 2.5 hours. Add N,O-di-methylhydroxylamine hydrochloride (18.8 g, 190 mmol) and stir at room temperature over night. Quench the reaction with water. Separate the phases and extract the water phase with t-butylmethylether (2×). Combine the organics and wash with 10% aqueous H₃PO₄, 20% aqueous KHCO₃, water and brine. Concentrate to afford 37.1 g (77%) of the title compound. MS (m/z)=203.1 [M−55]

Addition of Grignard to Weinreb Amide and Reduction of the Ketone to the Alcohol

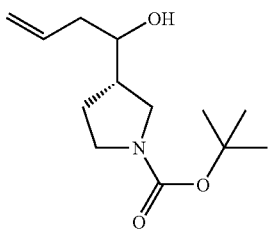

Add slowly and dropwise a solution of allylmagnesium bromide (2.0 M in THF, 100.3 mL, 200.5 mmol) to a stirred solution of (S)-3-(methoxy(methyl)carbamoyl)-pyrrolidine-1-carboxylic acid tert-butyl ester (37.0 g, 143.2 mmol) in THF (296 mL) kept under nitrogen at 0° C. Allow the reaction to warm to room temperature and continue to stir for 48 hours. Add the mixture over a cold solution (0-5° C.) of sodium borohydride (5.42 g, 143 mmol) and tertabutylammonium bromide (0.74 g, 2.39 mmol) in water (74 mL) and stir for 1 hour. Separate the phases and extract the water phase with t-butylmethylether (2×). Combine the organic phases and wash with water and brine. Concentrate and purify the crude residue by silica gel column chromatography eluting with t-butylmethylether/hexanes (3/7 to 7/3) to obtain (3S)-3-(1-hydroxy-but-3-enyl)-pyrrolidine-1-carboxylic acid tert-butyl ester (S-mix) (29 g, 85%). MS (m/z)=186.1 [M−55].

(3S)-3-(2-cyclopropyl-1-hydroxyethyl)pyrrolidine-1-carboxylic acid tert butyl ester (S-mix)

Add palladium (II) acetate (2.31 g; 0.298 mmol) to a stirred solution of (3S)-3-(1-hydroxy-but-3-enyl)-pyrrolidine-1-carboxylic acid tert-butyl ester (S-mix) (14.4 g, 59.7 mmol) in dichloromethane (43.2 mL). Add slowly a freshly prepared solution of diazomethane (100 mL, about 50 mmol in diethyl ether) under nitrogen at −30 to −40° C. (Caution: vigorous N₂ gas evolution). Evaporate the solvent and dissolve the crude in dichloromethane (43.2 mL). Add palladium (II) acetate (2.31 g, 0.298 mmol) followed by a freshly prepared solution of diazomethane (100 mL, about 50 mmol in diethyl ether) to the mixture kept under nitrogen at −30 to −40° C. (Caution: vigorous N₂ gas evolution). Evaporate the solvent and dissolve the crude in dichloromethane (43.2 mL). Add palladium (II) acetate (2.31 g, 0.298 mmol) followed by a freshly prepared solution of diazomethane (50 mL, about 25 mmol in diethyl ether) to the mixture kept under nitrogen at −30 to −40° C. (Caution: vigorous N₂ gas evolution). Evaporate the solvent, add hexanes (140 mL) to the crude residue and stir the suspension over night at room temperature. Filter the suspension over a pad of celite® and concentrate to obtain a quantitative yield (3S)-3-(2-cyclopropyl-1-hydroxyethyl)pyrrolidine-1-carboxylic acid tert butyl ester (S-mix). MS (m/z)=200.1 [M−55].

(3S)-3-[1-(6-Chloro-2-methyl-3-pyridyloxy)-2-cyclopropyl-ethyl]-pyrrolidine-1-carboxylic acid tert-butyl ester (S-1) and (S-2)

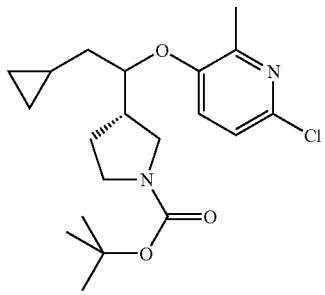

Add sodium hydride (60%, 6.20 g, 155.1 mmol) slowly to a mixture of (3S)-3-(2-cyclopropyl-1-hydroxy-ethyl)-pyrrolidine-1-carboxylic acid tert-butyl ester (S-mix) (19.8 g, 77.5 mmol), 6-chloro-3fluoro-2-methyl-pyridine (16.9 g, 116.3 mmol) and dimethylacetamide (59.4 mL) kept under an atmosphere of nitrogen at room temperature. Heat to 40° C. and stir for 3.5 hours. Cool the mixture and add methanol. Pour the mixture over 10% aqueous $H_3PO_4$ (100 mL)and t-butylmethylether (100 mL). Separate the phases and extract the water phase with t-butylmethylether (2×). Combine the organic phases and wash with water and brine. Evaporate the solvent to obtain a crude residue. Chromatograph the crude residue on silica gel eluting with t-butylmethylether/hexanes (2:8 to 4:6) to obtain a crude residue which was mixed with crude residue from another batch (based on 2 g of the alcohol). The mixture of diastereomers was separated by silica gel chromatography eluting with 25% of t-butylmethylether in hexanes to obtain (3S)-3-[1-(6-chloro-2-methyl-3-pyridyloxy)-2-cyclopropyl-ethyl]-pyrrolidine-1-carboxylic acid tert-butyl ester, isomer 1, (S-1) (15.0 g, 51%) as the first eluting isomer, MS (m/z)=325.0 (M−55) and (3S)-3-[1-(6-chloro-2-methyl-3-pyridyloxy)-2-cyclopropyl-ethyl]-pyrrolidine-1-carboxylic acid tert-butyl ester, isomer 2, (S-2) (12.0 mg, 41%) as the second eluting isomer. MS (m/z)=325.0 (M−55).

(3S)-3-[1-(6-chloro-2-methyl-3-pyridyloxy)-2-cyclopropyl-ethyl]-pyrrolidine, (S-1)

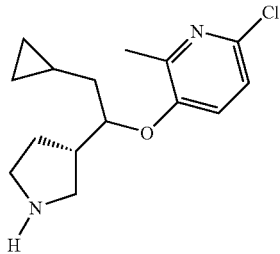

Add HCl (4M in 1,4-dioxane, 52.7 mL, 627 mmol) to a solution of (3S)-3-[1-(6-chloro-2-methyl-3-pyridyloxy)-2-cyclopropyl-ethyl]-pyrrolidine-1-carboxylic acid tert-butyl ester (S-1) (13.4 g, 35.2 mmol) in dichloromethane (40.2 mL). Stir under nitrogen at room temperature for 1 h. Evaporate the solvent and dissolve the residue in a mixture of t-butylmethylether (40 mL) and water (40 mL). Separate the phases, wash the aqueous phase with t-butylmethylether (2×). Adjust the pH of the aqueous phase to 9 by the addition of 10% aqueous $K_2CO_3$, extract with t-butylmethylether (3×). Wash the combined organic phases with water and brine. Evaporate the volatiles to obtain (3S)-3-[1-(6-chloro-2-methyl-3-pyridyloxy)-2-cyclopropyl-ethyl]-pyrrolidine (S-1) (9.6 g, 97%). MS (m/z)=281.2 [M+1]

(3S)-3-[1-(6-chloro-2-methyl-3-pyridyloxy)-2-cyclopropyl-ethyl]-pyrrolidine, L-tartrate (S-1)

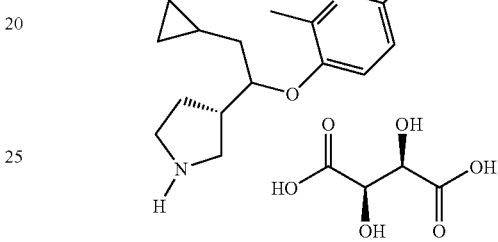

Add L-tartaric acid (5.1 g, 33.9 mmol) to a solution of (3S)-3-[1-(6-chloro-2-methyl-3-pyridyloxy)-2-cyclopropyl-ethyl]-pyrrolidine (S-1) (9.7 g, 34.5 mmol) in methanol (48.5 mL). Stir the mixture at room temperature for 15 minutes under nitrogen. Evaporate the volatiles, dissolve the residue in water (100 mL) and extract with t-butylmethylether (2×). Concentrate on the rotary evaporator the aqueous phase to a final volume of 50 mL while keeping the bath at 25° C. Lyophilize the residue to obtain 14.0 g, (95%) of the title compound. MS (m/z): 281.0 [M+1]

Assignment of Absolute Configuration of 3(S)-(1'-Hydroxy-3'-methyl-butyl)-pyrrolidine-1-carboxylic acid tert-butyl ester Isomers 1 and 2

There are two stereogenic carbons in 3(S)-(1'-hydroxy-3'-methyl-butyl)-pyrrolidine-1-carboxylic acid tert-butyl ester which correspond to carbons 5 and 7 (C5 and C7) as illustrated in FIG. 1.

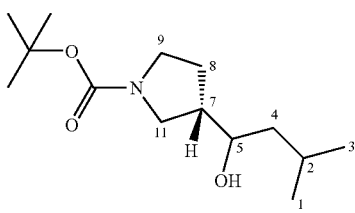

Figure 1

Because the configuration of C7 is known from the starting (S)—N-(tert-butoxycarbonyl)-pyrrolidine-3-carboxylic acid, the determination of relative configuration would lead to the assignment of the absolute configuration at C5. The relative configuration of flexible molecules can be accomplished if proton-carbon couplings are considered through the J-based configuration method described by Matsumori et al., J. Org. Chem. 64, 866 (1999). This approach involves the measurement of H—H and H—C couplings across a certain C—C bond and their conversion to dihedral angles via the Karplus-Altona relationship. The H—C couplings also follow a Karplus relationship, and small values, ranging from 1 to 3 Hz, are indicators of gauche orientations, and large values, ranging from 6 to 8 Hz, indicate anti arrangements.

The relevant H5-C11 proton-carbon coupling constant are measured using the satellite-selective 1D-TOCSY experiment described by P. Vidal, et al., J. Org. Chem., 72, 3166-3170 (2007). The 1D-TOCSY experiments in which the offset of the selective pulse are set on the low-frequency $^{13}C$ satellite of H11 are acquired. The resulting spectrum is compared with the conventional 1D-TOCSY experiment in which the H11 signal of the major 12C isotopomer is excited, or alternatively with the 1H spectrum. The three-bond H,C couplings between C11 and H5 is determined from the displacement of the relayed H5 signal in the satellite-selective TOCSY spectra relative to its position in the 1H spectrum, the coupling constant being twice the displacement. The coupling constant between C8 and H5 is not measured due to signal overlapping. The proton-proton and proton-carbon coupling constants across the C7-C5 bond are measured for each of 3(S)-(1-hydroxy-3-methyl-butyl)-pyrrolidine-1-carboxylic acid tert-butyl ester Isomer 1 and Isomer 2 prepared essentially as described in Preparation 4 and their values are in the following table.

| Compound | H—H or H—C Pair | $^3J$ (Hz) |
|---|---|---|
| Isomer 1 | H5—H7 | 7.0 |
| Isomer 1 | H5—C11 | 4.2 |
| Isomer 2 | H5—H7 | 7.0 |
| Isomer 2 | H5—C11 | 1.8 |

The small H5-C11 coupling constant in Isomer 2 indicates that H5 and C11 are gauche to each other in both populated conformers, which is consistent with the 3(S)-1'(S) isomer.

In vitro Transporter Affinity Assay

Human serotonin transporter (SERT), norepinephrine transporter (NET), or dopamine transporter (DAT) are cloned into a pcDNA3 vector and stably transfected into HEK293 cells. Membrane stocks are prepared following standard protocols, and $K_d$ values are calculated using saturation binding or homologous competition binding methods for each batch of membranes (Bylund and Toews, Am. J. Phys. (Lung Cell. Mold Physiol 9), 265, 421-429 (1993). All binding assays are conducted in 96-well plates using a method developed by converting a filtration radioligand binding assay to a scintillation proximity assay (SPA) format (Carpenter, et al., Methods in Molecular Biology, 190, 21-49 (2002)). Briefly, SERT membranes are used at a concentration of 10 µg/well in assay buffer containing 50 mM Tris, 150 mM NaCl, and 5 mM KCl (pH 7.4) in the presence of $^3$H-citalopram. Fluoxetine (100 µM) is used to determine non-specific binding, and venlafaxine is used as a positive control. NET membranes are used at a concentration of 8 µg/well in assay buffer containing 50 mM Tris, 300 mM NaCl, and 5 mM KCl (pH 7.4). $^3$H-Nisoxetine is used as the tracer, 100 µM desipramine serves as a measure of non-specific binding, and nisoxetine is used as the positive control. For DAT binding assays, the assay buffer is the same as for SERT, membranes are used at 20 µg/well, 100 µM nomifensine is used to determine non-specific binding, $^3$H-WIN 35428 (Perkin Elmer) serves as the radiotracer, and nomifensine is used as the positive control. In all cases, 0.5 mg/well of wheat-germ agglutinin scintillation proximity assay beads (WGA-SPA, GE Health Sciences) are used to capture the membranes, and plates are incubated for 3 hours at room temperature. Radioactivity is measured and $K_i$ values calculated using a four-parameter logistic curve fitting program (ActivityBase v5.3.1.22).

Exemplified compounds are tested essentially as described above and are found to have high affinity for the hSERT and hNET receptors, but much lower affinity for the hDAT receptor in vitro. $K_i$ for SERT and NET are found to be less than 20.1 nM and 23.4 nM, respectively, while the $K_i$ for DAT is found to be greater than 255 nM. The compound of EXAMPLE 19 is tested essentially as described above and is found to have affinities as shown in the table below.

| RECEPTOR | $K_i$ (nM) |
|---|---|
| hSERT | 0.199 ± 0.02 (n = 6) |
| hNET | 1.08 ± 0.32 (n = 6) |
| hDAT | 461 ± 72 (n = 6) |

(mean ± std error)

In vitro Inhibitor Activity Assay

Human serotonin (SERT) or norepinephrine (NET) transporters are cloned into a pcDNA3 vector and stably transfected into HEK293 cells. Both assays are modified from methods described by Eshleman et al., J. Pharmacol. Exptl Ther., 289, 877-885 (1999)) and Wall et al., Mol. Pharmacol., 47, 544-550 (1995). Cells are grown on poly-D-lysine coated flasks or 96-well plates in D-MEM/F-12 3:1 (3 part of Dulbecco's Modified Eagle Medium in 1 part of Nutrient Mix F-12 medium) containing 5% fetal bovine serum, 250 µg/mL geneticin, and 20 mM Hepes. Cells are plated at 40,000 cells per well in 200 µL of medium and incubated for 18-24 hours at 37° C. prior to the assay. The assay uptake buffer consists of Krebs-Ringer bicarbonate stock supplemented with 1.26% sodium bicarbonate, 20 mM HEPES, and 100 µM each of pargyline and ascorbic acid. Following a 30 minute pre-incubation with the compound or indatraline (as a positive control), $^3$H-serotonin or $^3$H-norepinephrine is added for 1 min. and 50 sec. The $^3$H-substrate is then removed, and the cells washed 4x with 100 µL of cold uptake buffer using multimek. Triton X-100 (1%) is added to lyse the cells and, after mixing, all the contents are transferred to a white-bottom plate. Microscint™ 40 is added to each well and the radioactivity is quantitated for 1 min. per well. Results are analyzed as $IC_{50}$ values using a four-parameter logistic curve fitting program (ActivityBase v5.3.1.22).

Exemplified compounds are tested essentially as described above and are found to be inhibitors of serotonin and norepinephrine reuptake, having $IC_{50}$ of SERT and NET of less than 227 nM and 44.6 nM, respectively. The compound of EXAMPLE 19 is tested essentially as described above and is found to be an inhibitor of serotonin and norepinephrine reuptake in vitro, having $IC_{50}$'s as shown in the table below.

| RECEPTOR | $IC_{50}$ (nM) |
|---|---|
| hSERT | 2.15 ± 0.70 (n = 4) |
| hNET | 7.34 ± 1.48 (n = 4) |

(mean ± std error)

In vivo Transporter Occupancy Assay

Male Sprague-Dawley rats weighing 240-280 gm in groups of three are used to determine serotonin transporter occupancy. Animals are fasted at least 12 hr. before the start of each experiment. Animals are orally administered vehicle or 0.10, 0.33, 1.00, 3.33 or 10.00 mg/kg doses of test compound in 4% Glucose in 25 mM Phosphate buffer, (pH=3.0) containing 0.1, 0.33, 1, 3.33, or 10% CAPTISOL™ (concentration of CAPTISOL™ (%)=dose of test compound (mg/kg)). After 2 hr., animals are intravenously administered N,N-dimethyl-2-(2-amino-4-cyanophenylthio)-benzylamine (10 µg/kg) in saline in the lateral tail vein. After an additional 40 min., rats are sacrificed via cervical dislocation, and a portion of the frontal cortex is removed and placed on dry ice. An additional control group of three rats is dosed with paroxetine maleate at 12 mg/kg, i.v., followed by N,N-dimethyl-2-(2-amino-4-cyanophenylthio)-benzylamine (10 µg/kg) 1 hr. later.

Tissues are allowed to thaw and then four volumes (w/v) of acetonitrile containing 0.1% formic acid is added. Samples are homogenized using an ultrasonic dismembrator probe and centrifuged for 16 min. at 14,000×g. One volume of the supernatant is added to 3 volumes of water in an autosampler vial and vortexed. Separation is achieved with a Zorbax C18 HPLC column and a mobile phase gradient of from 20% to 90% acetonitrile/water, each with 0.1% formic acid. The total HPLC run time is 3.5 min with an additional 2.0 min re-equilibration time. An API4000 triple quadrupole mass spectrometer (Applied Biosystems, Foster City, Calif., USA) operating in MRM mode is used for detection. The ion transition monitored is 284.1/239.1 m/z for N,N-dimethyl-2-(2-amino-4-cyanophenylthio)-benzylamine.

The level of N,N-dimethyl-2-(2-amino-4-cyanophenylthio)-benzylamine (tracer) in the cortex of vehicle-pretreated animals represents the sum of nonspecific and specific binding and is assigned the value of 0% occupancy (all receptors available to the tracer). The lower level of tracer in animals pretreated with the very high intravenous dose of paroxetine maleate, the positive control group, represents the nonspecific binding and is assigned the value of 100% occupancy (no receptors available to the tracer). Levels of tracer in the cortex following oral administration of test compound are interpolated linearly between these two extremes in order to determine the percent serotonin transporter occupancy. Data are expressed as means±SEM (n=3/group) calculated using Prism version 3.0 (GraphPad Software Inc., San Diego, Calif., USA). The $ED_{80}$ values are obtained by fitting the data to a sigmoidal curve using nonlinear regression.

The compound of EXAMPLE 19 is tested essentially as described above and is found to have an absolute $ED_{80}$ of 7.1 mg/kg, based on the below dose response data for 1 hr. post dosing, thus confirming occupancy of serotonin receptors in vivo.

| Dose (mg/kg p.o.) | % Occupancy | S.E.M. |
|---|---|---|
| 30 | 105.6 | 1.8 |
| 10 | 94.0 | 3.6 |
| 3 | 43.3 | 5.8 |
| 1 | 25.0 | 4.2 |
| 0.3 | 5.9 | 3.9 |
| $ED_{80}$ | 7.1 mg/kg | |

Alpha MMT: Monoamine Depletion Inhibition Assay

Neurotransmitter transporter inhibitors can prevent the depletion of brain monoamines when the depleting agent requires active uptake into neurons via a transporter. DL-Para-chloroamphetamine (PCA) is transported into serotonergic neurons via the neuronal transporter and produces a long-lasting depletion of rat brain serotonin (5-HT) concentrations. Alpha-methyl-m-tyrosine (α-MMT) is a noradrenergic depleting agent that is β-hydroxylated to metaraminol in vivo and actively transported into norepinephrine (NE) neurons via the neuronal transporter producing a decrease in NE levels in rat brain. The depletion of rat brain 5-HT levels by PCA and rat cortical NE concentrations by α-MMT is blocked by agents with 5-HT and NE reuptake inhibitor activity. Compounds of the present invention may be assayed for their activity to prevent the depletion of rat brain 5-HT concentrations by PCA and the depletion of rat cortical NE concentrations by a-MMT in fed and fasted rats in vivo using the following methods.

Male Sprague Dawley rats weighing 160-180 grams are fasted overnight or allowed food ad libitum. Animals are gavaged with vehicle (sterile $H_2O$) or test compound 2 hr. prior to administration of 10 mg/kg PCA hydrochloride (ip) or 6.25 mg/kg α-MMT (sc). All compounds are administered at 1 mL/kg. Animals are sacrificed 2 hr. after PCA or α-MMT administration. Tissues are dissected, frozen on dry ice and stored at −70° prior to analysis. For animals administered PCA, whole brain serotonin (5-HT) concentrations are measured using high-pressure liquid chromatography with electrochemical detection as described by Fuller and Perry in *J. Pharmacol. Exp. Ther.*, 248, 50-56 (1989). For animals administered a-MMT, cortical norepinephrine concentrations are measured by HPLC-EC after alumina absorption as described by Bymaster, et al., *Neuropsychopharmacology*, 27(5), 699-711 (2002). The data are collected using an EZChrom™ chromatography data system (Scientific Software, San Ramon, Calif.) which calculates peak heights and sample concentrations. Analysis of variance, followed by Tukey's Honestly Significant Difference test post hoc, identifies significant differences between treatment groups ($P \leq 0.05$). Doses that antagonized the PCA- or α-MMT-induced depletion of monoamines by 50 percent, ($ED_{50}$'s) are calculated using a best-fit linear regression analysis.

The compound of EXAMPLE 19 is tested essentially as described above and is found to antagonize α-MMT induced depletion of norepinephrine in rat cortex with an $ED_{80}$ of 9.5 mg/kg as based on the dose responses below, thus confirming in vivo efficacy at inhibiting norepinephrine transporter function.

| Dose (mg/kg p.o.) | % Inhibition | S.E.M. |
|---|---|---|
| 30 | 115.3 | 14.6 |
| 10 | 79.0 | 9.3 |
| 3 | 21.0 | 5.5 |
| 1 | 5.6 | 3.9 |
| 0.3 | 7.0 | 10.4 |
| $ED_{80}$ | 9.5 mg/kg | |

Manual Formalin Test

The manual formalin test is performed in custom-made Plexiglas boxes approx. 25 cm×25 cm×20 cm in size. A mirror placed at the back of the cage allows the unhindered observation of the formalin injected paw. Rats (Charles River (CRL) Sprague Dawley (SD)) are placed individually in the cubicles at least 30 min. prior to the experiment. All testing is conducted between 08:00 and 14:00 h and the testing room temperature is maintained at 21-23° C. Peripherally administered test compounds are dosed at varying times before the formalin challenge. Formalin (50 μL of a 5% solution in saline) is injected subcutaneously into the dorsal lateral surface of the right hind paw with a 27 gauge needle. Observation starts immediately after the formalin injection. Formalin induced pain is quantified by recording the number of seconds each licking event lasts in 5 min. intervals. The pain scoring is measured for 50 min. after the formalin injection. Two phases of pain behavior are observed as previously described (Wheeler-Aceto, H., Porreca, F. and Cowan, A., The rat paw formalin test: comparison of noxious agents, Pain 40 (1990) 229-238.). The early phase starts immediately after the formalin injection and lasts approximately 5 min., followed by the late phase that starts between minutes 10-15 with a maximum response typically observed around 25-35 min. after the formalin injection. After the 50 min. observation period, animals are sacrificed with $CO_2$.

Of the different scoring parameters reported for the formalin test, the total time spent licking and biting the injected paw is considered to be most relevant. (Abbott et al., *The formalin test: scoring properties of the first and second phases of the pain response in rats*, Pain 60 (1995) 91-102; Coderre et al., *The formalin test: a validation of the weighted-scores method of the behavioral pain rating*, Pain 54 (1993) 43-50).) The early phase score is the sum of time spent licking (seconds) from time 0 to 5 min. The late phase score is obtained by adding the total number of seconds spent licking from minute 16 to min. 40 of the observation period. Data are presented as means with standard errors of means (±SEM). Data is evaluated by one-way analysis of variance (ANOVA) and the appropriate contrasts analyzed by Dunnett "t' test for two sided comparisons. Differences are considered to be significant if the P-value is less than 0.05. (Abbott, supra.; Coderre, supra.; and Wheeler-Aceto, supra.)

The compound of EXAMPLE 19 is tested essentially as described above and is found to significantly reduce pain behavior with an $ED_{50}$ of 13.4 mg/kg deriving from the following dose responses:

| Dose (mg/kg p.o.) | % reduction in total time licking | S.E.M. |
| --- | --- | --- |
| 30 | 78.4 | 5.6% |
| 10 | 38.0 | 7.8% |
| 3 | 14.4 | 13.0% |
| 1 | 4.5 | 8.3% |
| $ED_{50}$ | 13.4 mg/kg | |

While it is possible to administer compounds employed in the methods of this invention directly without any formulation, the compounds are usually administered in the form of pharmaceutical compositions comprising at least one compound of Formula I, or a pharmaceutically acceptable salt thereof, as an active ingredient and at least one pharmaceutically acceptable carrier, diluent and/or excipient. These compositions can be administered by a variety of routes including oral, intranasal, transdermal, subcutaneous, intravenous, intramuscular, and pulmonary. Such pharmaceutical compositions and processes for preparing them are well known in the art. See, e.g., Remington: The Science and Practice of Pharmacy (University of the Sciences in Philadelphia, ed., 21$^{st}$ ed., Lippincott Williams & Wilkins Co., 2005).

The compositions are preferably formulated in a unit dosage form, each dosage containing from about 0.1 to about 500 mg, more usually about 1.0 to about 200 mg, as for example between about 1 and 20 mg of the active ingredient. The term "unit dosage form" refers to physically discrete units suitable as unitary dosages for human subjects and other mammals, each unit containing a predetermined quantity of active material calculated to produce the desired therapeutic effect, in association with at least one suitable pharmaceutically acceptable carrier, diluent and/or excipient.

The compounds of Formula I are generally effective over a wide dosage range. For example, dosages per day normally fall within the range of about 0.001 to about 30 mg/kg, more usually from about 0.01 to 3.0 mg/kg, and as for example between 0.01 and 0.3 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:

1. The compound of the formula:

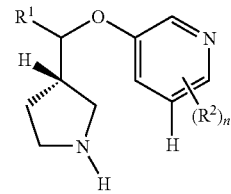

or a pharmaceutically acceptable salt thereof,
wherein $R^1$ is selected from the group consisting of n-propyl, isobutyl, $(C_3-C_4)$cycloalkyl, and $(C_3-C_4)$cycloalkyl-methyl-;
n is 1 or 2; and
each $R^2$ is independently selected from the group consisting of fluoro, chloro, bromo, methyl, ethyl, trifluoromethyl, methoxy, ethoxy, cyclopropylmethyloxy, trifluoromethoxy, methylamino, cyclopropylamino and t-butylcarbonylamino, provided that when n is 2, at least one of $R^2$ is fluoro, chloro, bromo, methyl, ethyl, trifluoromethyl, methoxy, or ethoxy.

2. The compound of claim 1 wherein $R^1$ is n-propyl or isobutyl, or a pharmaceutically acceptable salt thereof.

3. The compound of claim 1 wherein $R^1$ is isobutyl, or a pharmaceutically acceptable salt thereof.

4. The compound of claim 1 wherein $R^1$ is $(C_3-C_4)$cycloalkyl or $(C_3-C_4)$cycloalkyl-methyl-, or a pharmaceutically acceptable salt thereof.

5. The compound of claim 1 which is (S)-3-((S)-1-(6-Methoxy-2-methyl-3-pyridyloxy)-3-methyl-butyl)-pyrrolidine, or a pharmaceutically acceptable salt thereof.

6. A pharmaceutical composition comprising a compound of the formula:

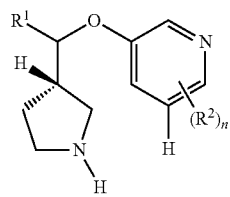

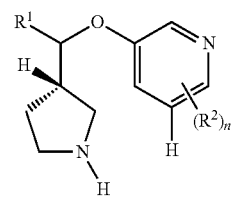

or a pharmaceutically acceptable salt thereof, wherein $R^1$ is selected from the group consisting of n-propyl, isobutyl, $(C_3-C_4)$cycloalkyl, and $(C_3-C_4)$cycloalkyl-methyl-;

n is 1 or 2; and each $R^2$ is independently selected from the group consisting of fluoro, chloro, bromo, methyl, ethyl, trifluoromethyl, methoxy, ethoxy, cyclopropylmethyloxy, trifluoromethoxy, methylamino, cyclopropylamino and t-butylcarbonylamino, provided that when n is 2, at least one of $R^2$ is fluoro, chloro, bromo, methyl, ethyl, trifluoromethyl, methoxy, or ethoxy, in combination with a pharmaceutically acceptable carrier, diluent, or excipient.

7. A method of treating chronic pain in a mammal comprising administering to a mammal in need of such treatment an effective amount of a compound of the formula:

or a pharmaceutically acceptable salt thereof, wherein $R^1$ is selected from the group consisting of n-propyl, isobutyl, $(C_3-C_4)$cycloalkyl, and $(C_3-C_4)$cycloalkyl-methyl-;

n is 1 or 2; and each $R^2$ is independently selected from the group consisting of fluoro, chloro, bromo, methyl, ethyl, trifluoromethyl, methoxy, ethoxy, cyclopropylmethyloxy, trifluoromethoxy, methylamino, cyclopropylamino and t-butylcarbonylamino, provided that when n is 2, at least one of $R^2$ is fluoro, chloro, bromo, methyl, ethyl, trifluoromethyl, methoxy, or ethoxy.

8. The method of claim 7 where the mammal is a human.

9. The method of claim 7 where the compound is (S)-3-((S)-1-(6-Methoxy-2-methyl-3-pyridyloxy)-3-methyl-butyl)-pyrrolidine, or a pharmaceutically acceptable salt thereof.

10. The method of claim 9 where the mammal is a human.

* * * * *